US011602404B2

United States Patent
Arai et al.

(10) Patent No.: US 11,602,404 B2
(45) Date of Patent: Mar. 14, 2023

(54) MEDICAL SUPPORT ARM APPARATUS

(71) Applicant: SONY CORPORATION, Tokyo (JP)

(72) Inventors: Jun Arai, Kanagawa (JP); Yasuhisa Kamikawa, Tokyo (JP); Wataru Kokubo, Tokyo (JP); Yasuhiro Matsuda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 806 days.

(21) Appl. No.: 16/339,487

(22) PCT Filed: Oct. 24, 2017

(86) PCT No.: PCT/JP2017/038399
§ 371 (c)(1),
(2) Date: Apr. 4, 2019

(87) PCT Pub. No.: WO2018/088203
PCT Pub. Date: May 17, 2018

(65) Prior Publication Data
US 2019/0328475 A1 Oct. 31, 2019

(30) Foreign Application Priority Data

Nov. 8, 2016 (JP) .............................. JP2016-217751

(51) Int. Cl.
*A61B 34/30* (2016.01)
*A61B 34/00* (2016.01)
*A61B 34/20* (2016.01)

(52) U.S. Cl.
CPC .............. *A61B 34/70* (2016.02); *A61B 34/20* (2016.02); *A61B 34/30* (2016.02); *A61B 2034/2055* (2016.02); *A61B 2034/301* (2016.02)

(58) Field of Classification Search
CPC ......... A61B 34/30; A61B 34/20; A61B 34/70; A61B 2034/2055; A61B 2034/301
See application file for complete search history.

(56) References Cited

U.S. PATENT DOCUMENTS 5,372,147 A * 12/1994 Lathrop, Jr. ........... A61B 34/30
600/230
5,397,323 A * 3/1995 Taylor .................... A61B 34/71
901/41

(Continued)

FOREIGN PATENT DOCUMENTS

| CN | 103144692 A | 6/2013 |
| CN | 104546066 A | 4/2015 |

(Continued)

OTHER PUBLICATIONS

International Search Report dated Jan. 29, 2018 in PCT/JP2017/038399 filed on Oct. 24, 2017 4 pages.

*Primary Examiner* — Stephen Holwerda
(74) *Attorney, Agent, or Firm* — Xsensus LLP

(57) ABSTRACT

A medical support system that includes a support arm including one or more active joints having an actuator, and one or more passive coupling mechanisms including a passive joint and a telescopic extension arm, the passive joint having no actuator; and processing circuitry configured to obtain information indicating a change due to movement of the one or more passive coupling mechanisms, and control the actuator of each of the one or more active joints based on the obtained information indicating the change, and the telescopic extension arm is positioned between (1) an active joint of the one or more active joints on a first side of the telescopic extension arm, and (2) the passive joint on a second side of the telescopic extension arm, the first side (Continued)

being closer to an proximal end of the support arm than a distal end of the support arm.

17 Claims, 13 Drawing Sheets

(56) References Cited

U.S. PATENT DOCUMENTS

| | | | |
|---|---|---|---|
| 5,626,595 A * | 5/1997 | Sklar | A61B 17/320016 606/180 |
| 5,647,373 A * | 7/1997 | Paltieli | A61B 34/70 600/461 |
| 5,887,121 A | 3/1999 | Funda et al. | |
| 6,226,566 B1 | 5/2001 | Funda et al. | |
| 6,723,106 B1 * | 4/2004 | Charles | B25J 9/1065 606/130 |
| 2001/0001132 A1 | 5/2001 | Funda et al. | |
| 2003/0082041 A1 * | 5/2003 | Barney | B66F 9/0655 414/685 |
| 2004/0024311 A1 * | 2/2004 | Quaid | A61B 90/36 600/428 |
| 2004/0236352 A1 | 11/2004 | Wang et al. | |
| 2006/0280587 A1 * | 12/2006 | Guerra | B25J 9/104 414/749.1 |
| 2009/0139119 A1 * | 6/2009 | Janardhan | G01G 19/021 37/413 |
| 2014/0052154 A1 * | 2/2014 | Griffiths | B25J 9/1633 606/130 |
| 2017/0176704 A1 | 6/2017 | Hirose et al. | |
| 2017/0181801 A1 | 6/2017 | Griffiths et al. | |

FOREIGN PATENT DOCUMENTS

| | | |
|---|---|---|
| JP | 2006-61272 A | 3/2006 |
| JP | 2009-95959 A | 5/2009 |
| JP | 2009-269102 A | 11/2009 |
| JP | 2010-188471 A | 9/2010 |
| JP | 2011-209099 A | 10/2011 |
| WO | WO 2015/046081 A1 | 4/2015 |
| WO | WO 2015/127078 A1 | 8/2015 |
| WO | 2015/137038 A | 9/2015 |
| WO | WO 2016/017532 A1 | 2/2016 |

* cited by examiner

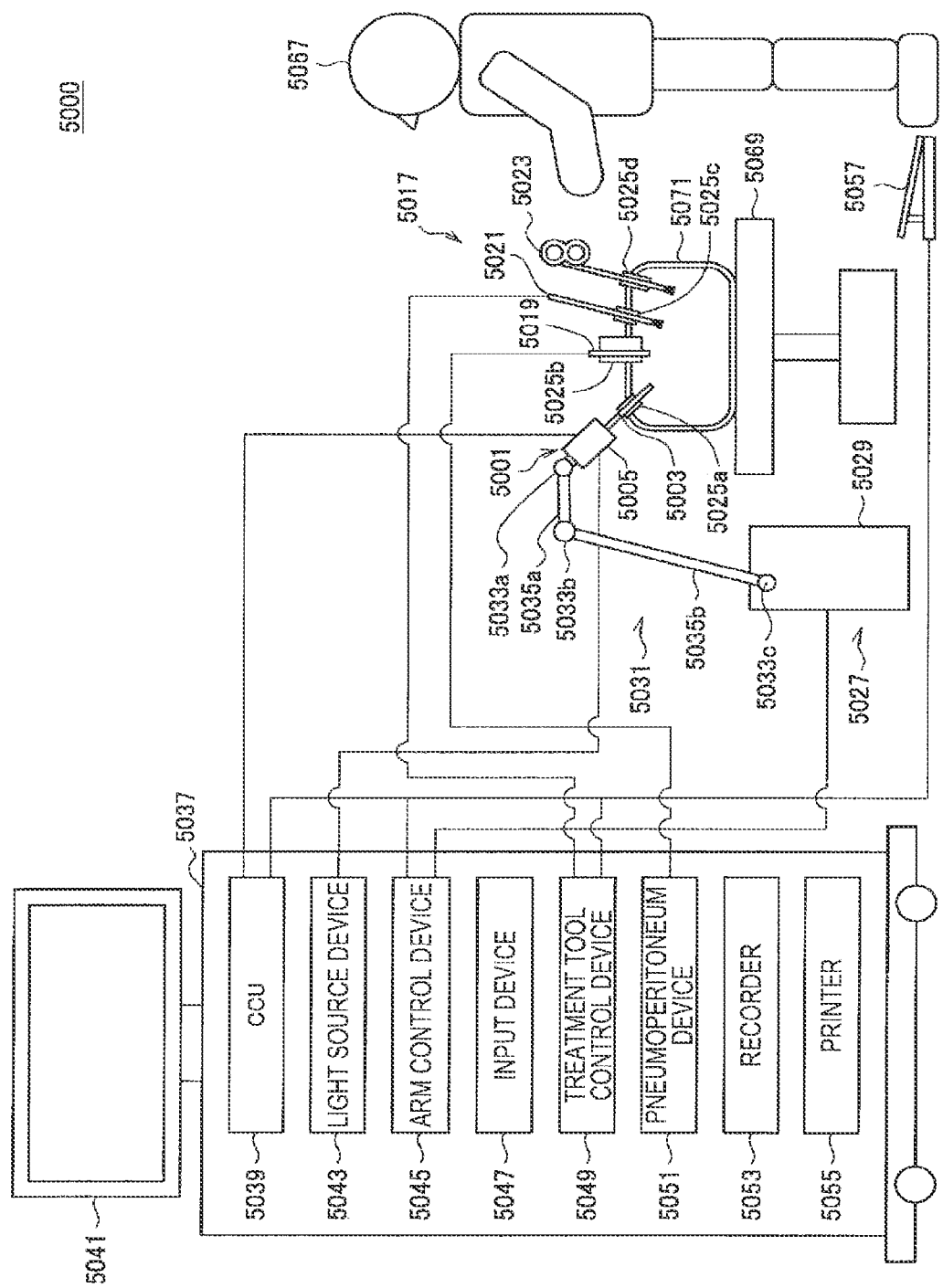
[Fig. 1]

[Fig. 2]
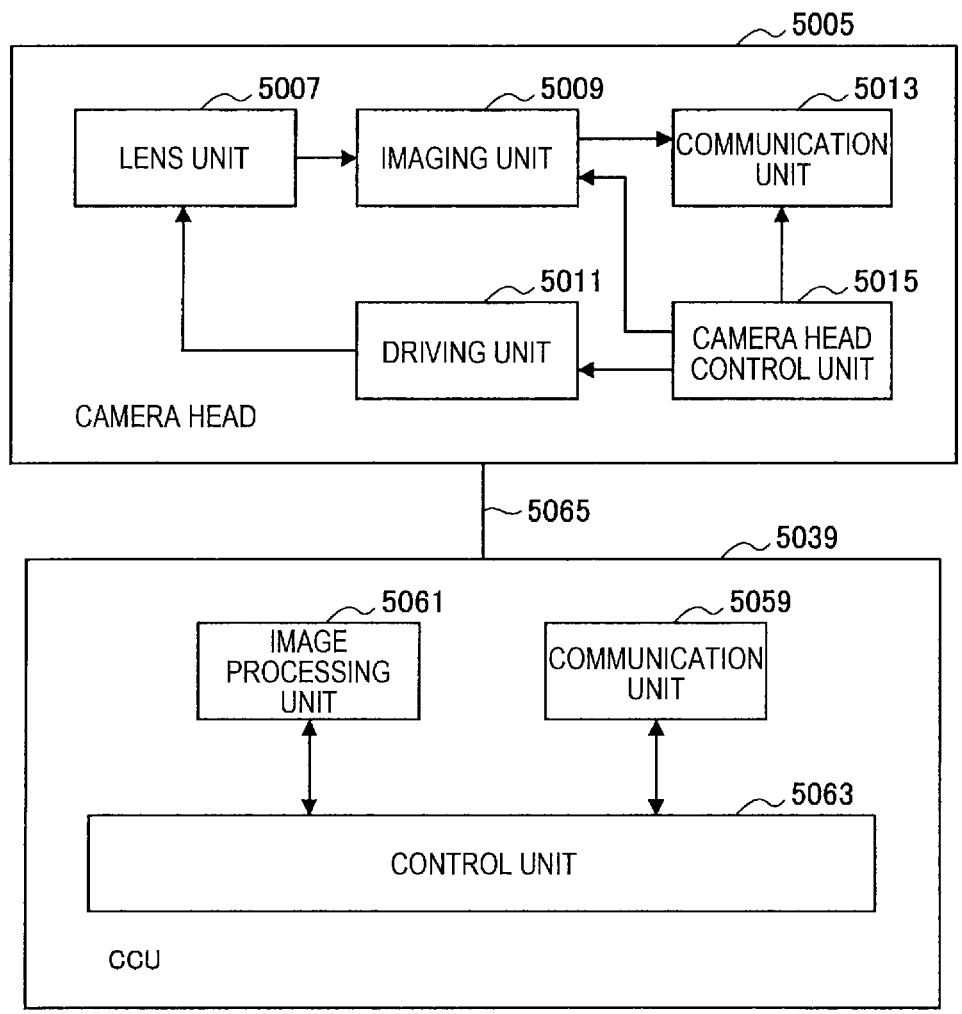

[Fig. 3]
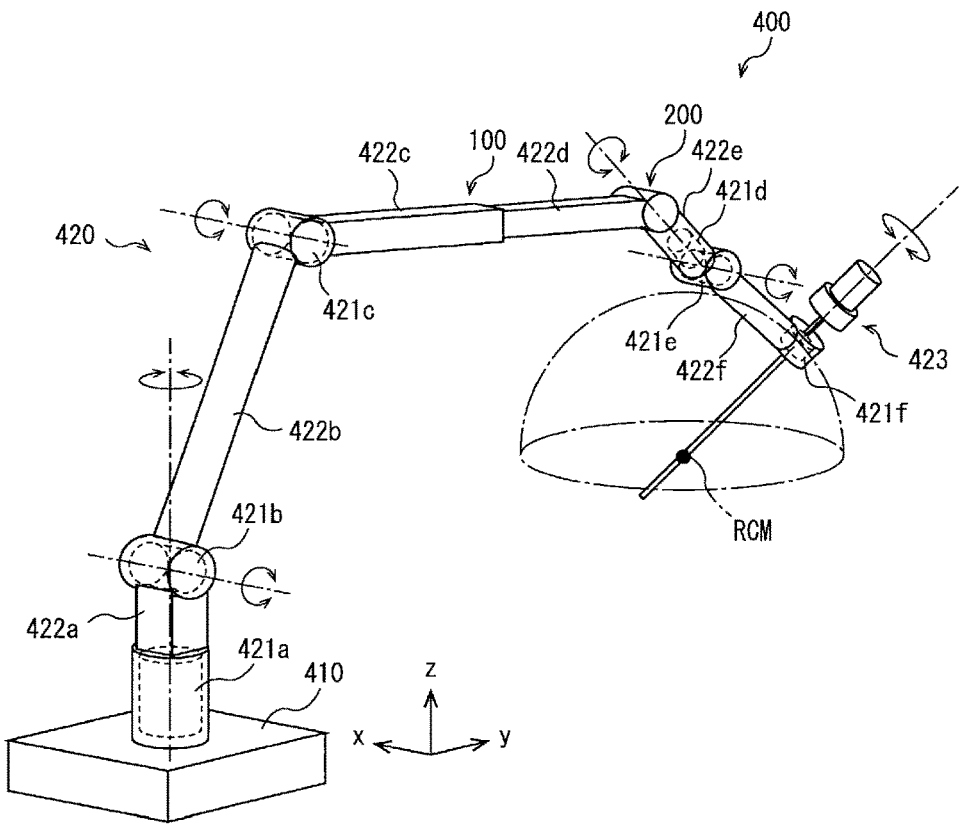
[Fig. 4]
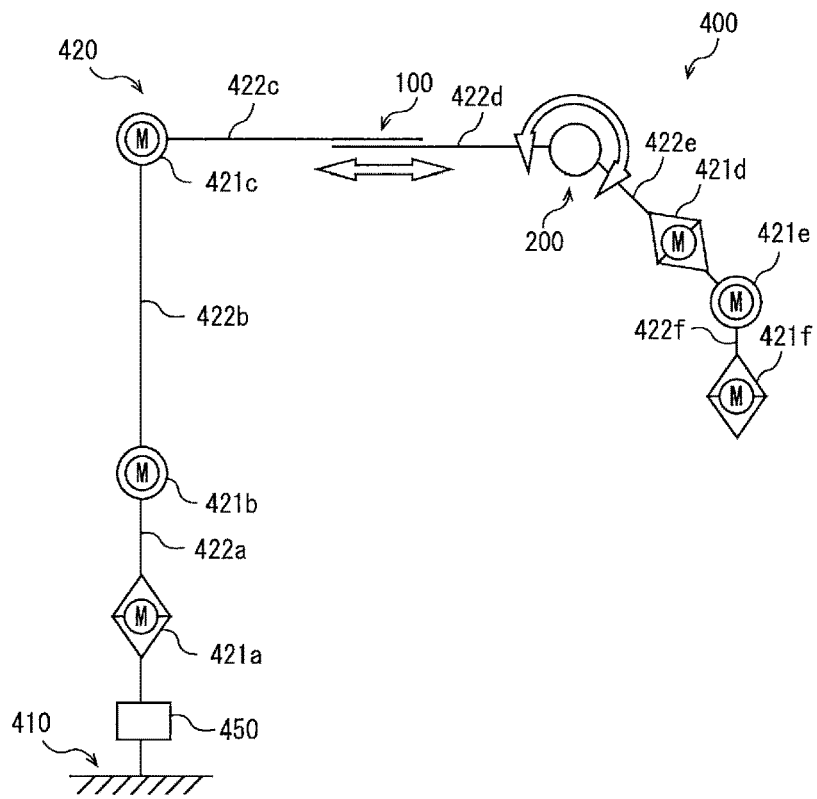

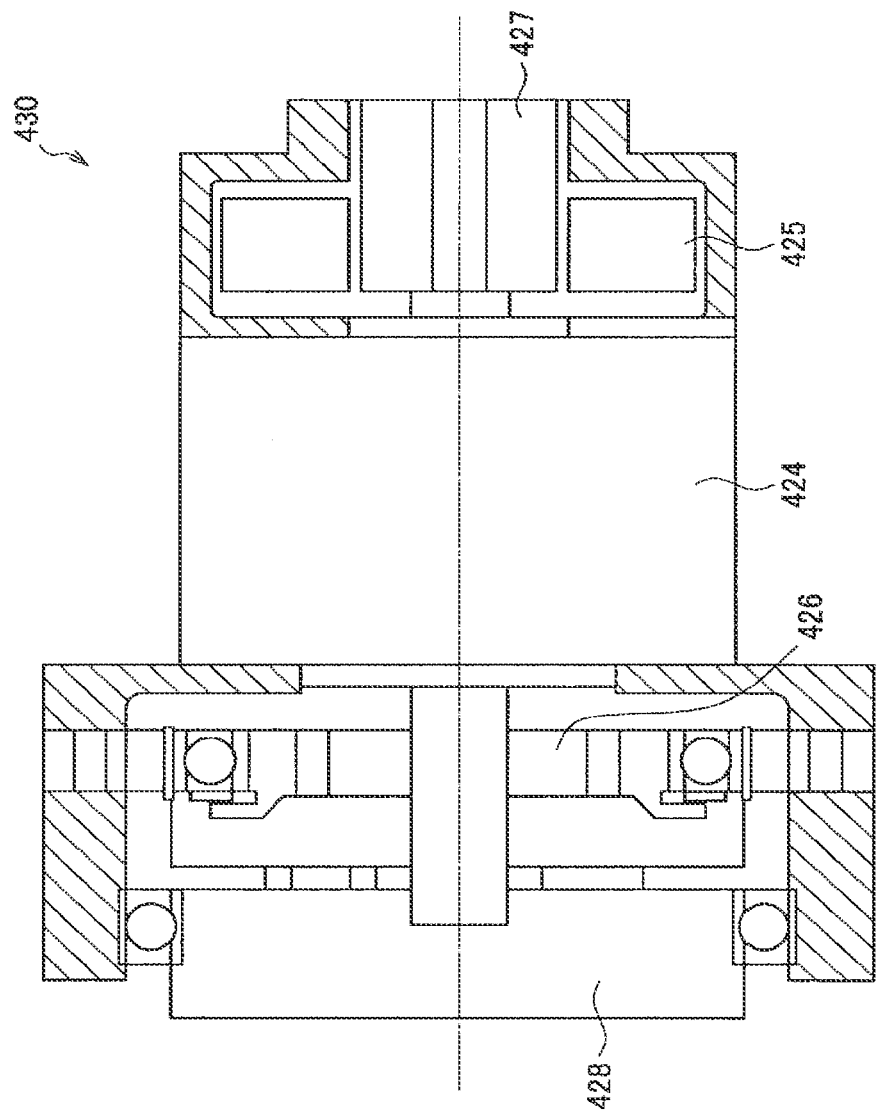
[Fig. 5]

[Fig. 6]
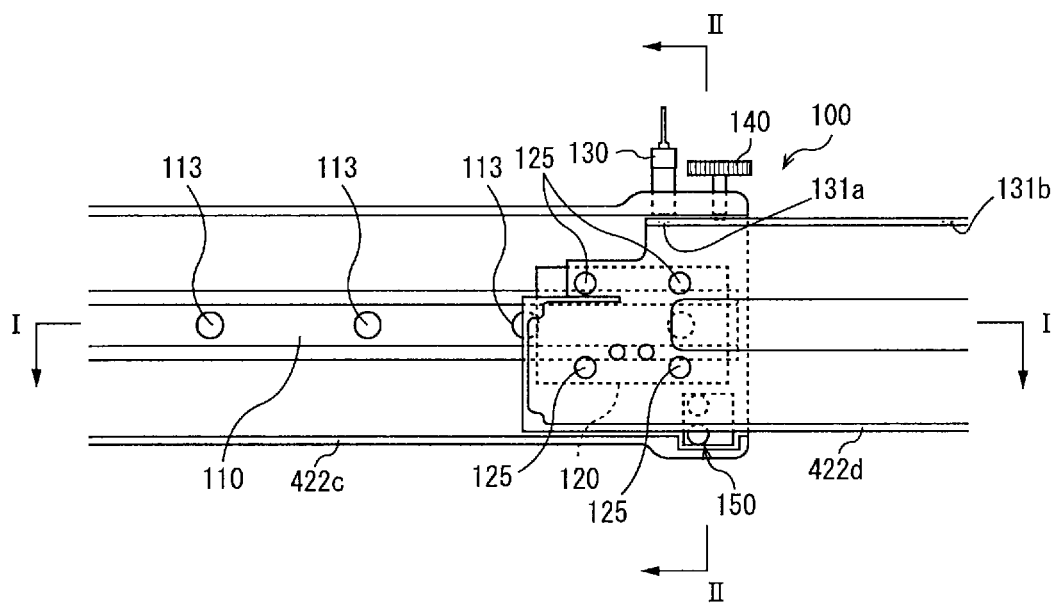
[Fig. 7]
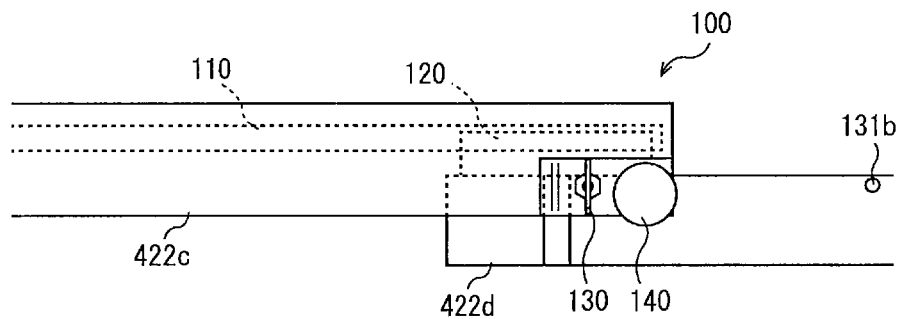
[Fig. 8]
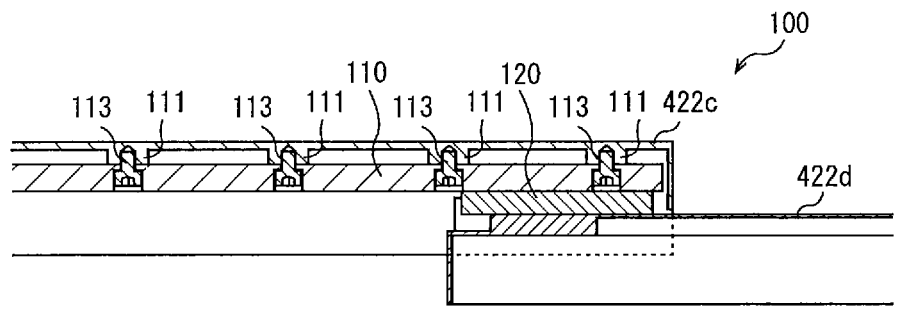

[Fig. 9]
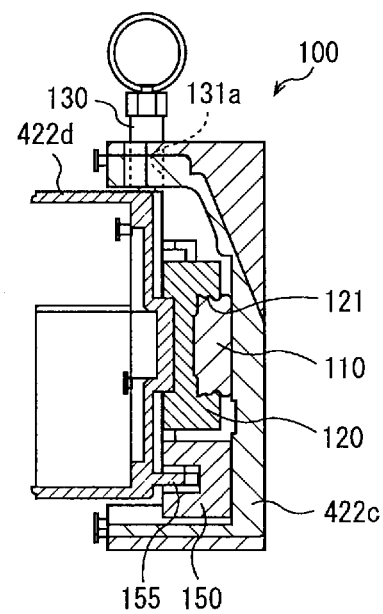
[Fig. 10]
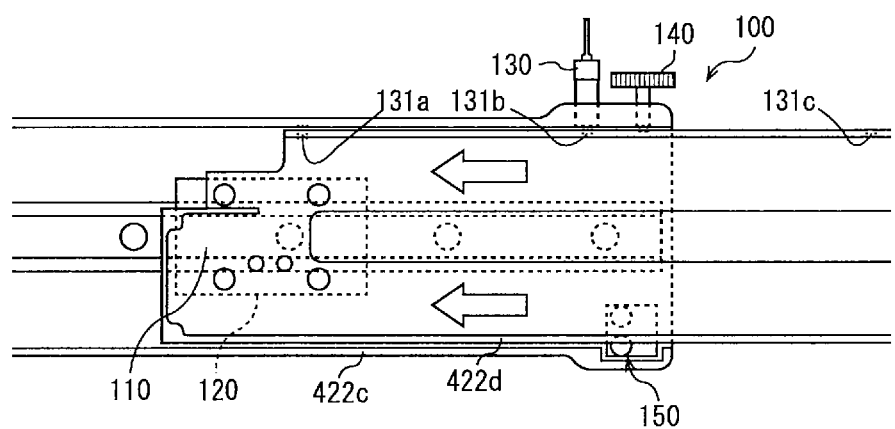

[Fig. 11]
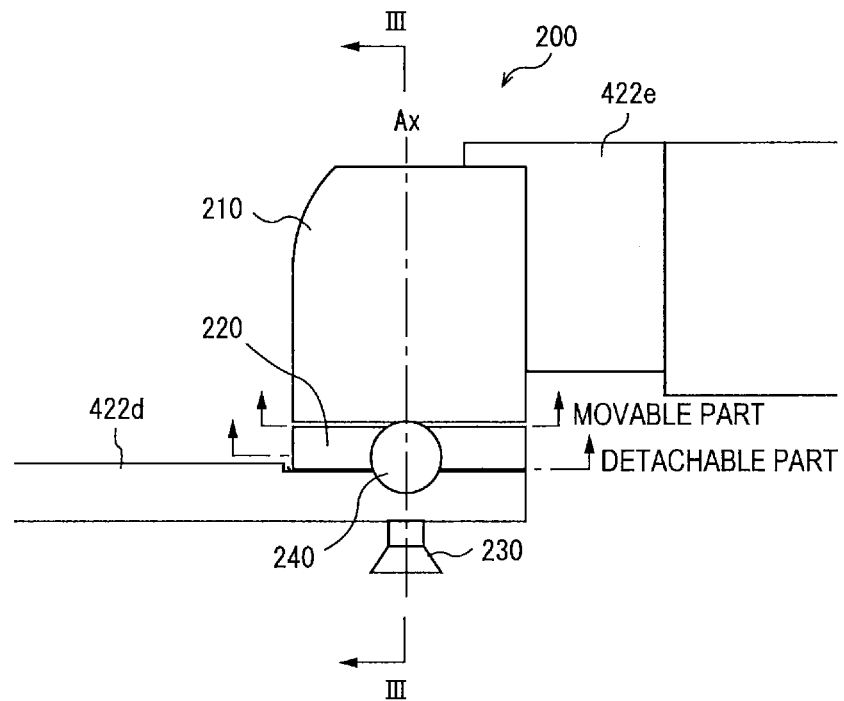
[Fig. 12]
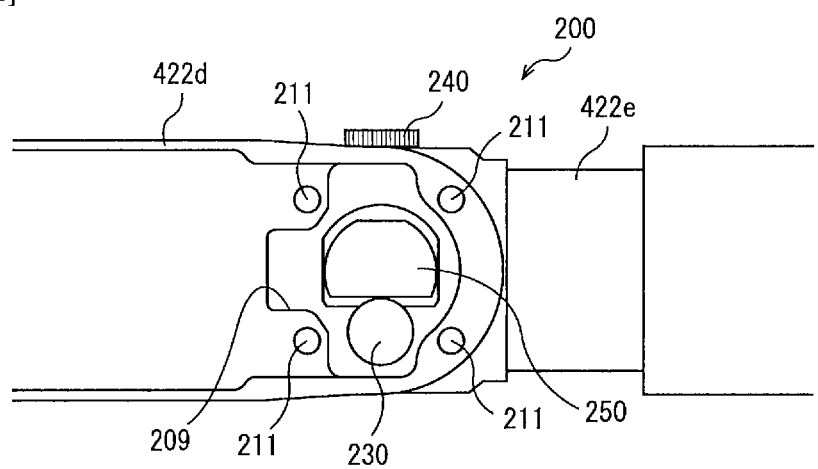

[Fig. 13]
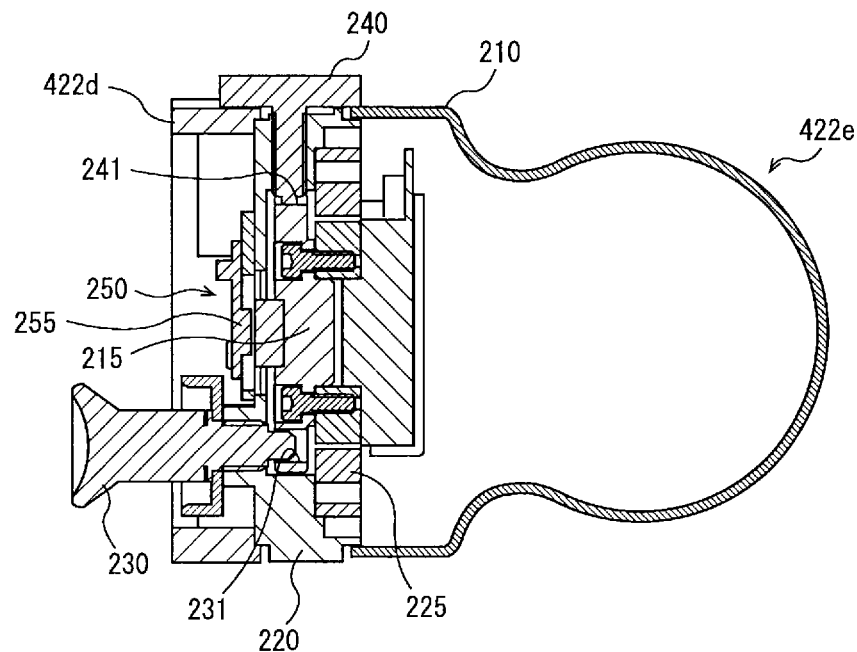
[Fig. 14]
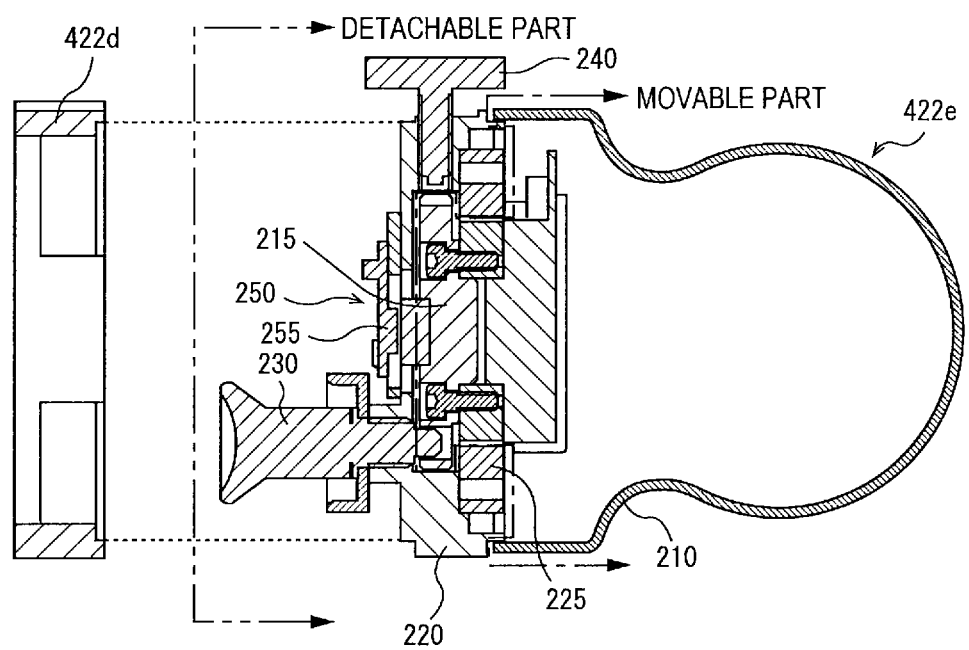

[Fig. 15]
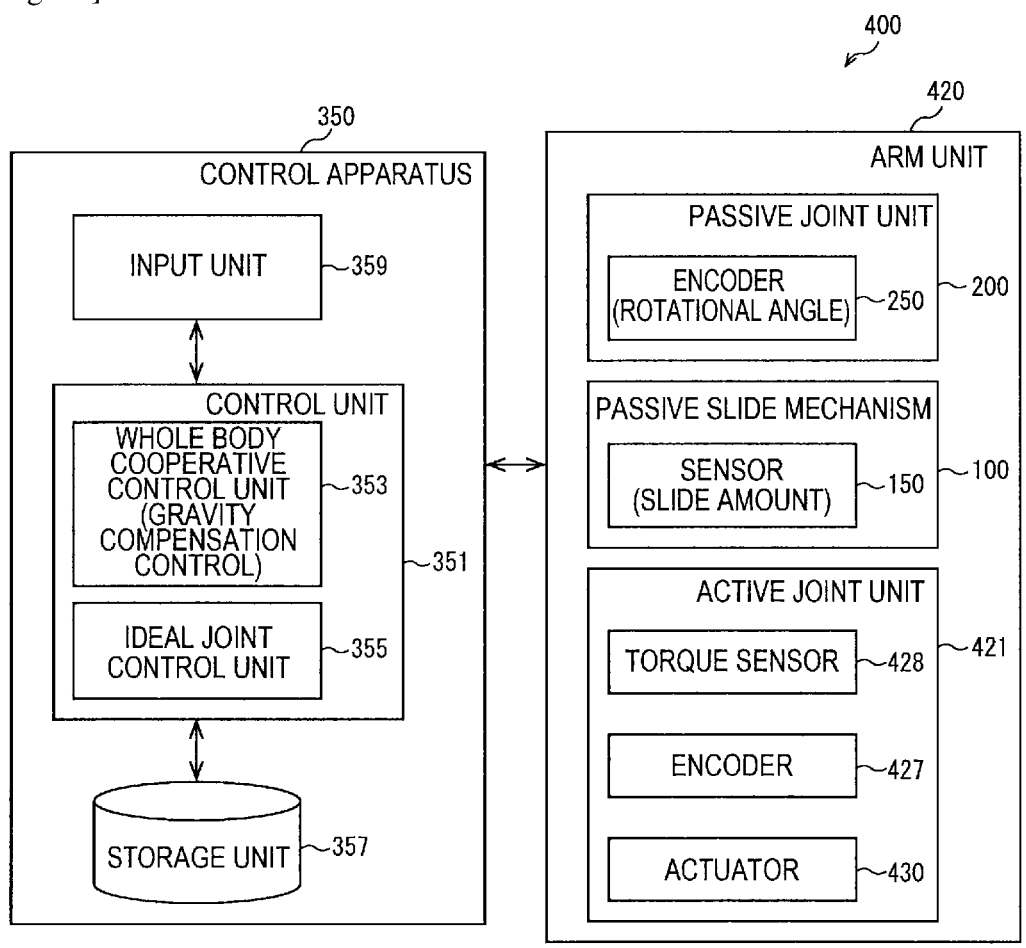

[Fig. 16]
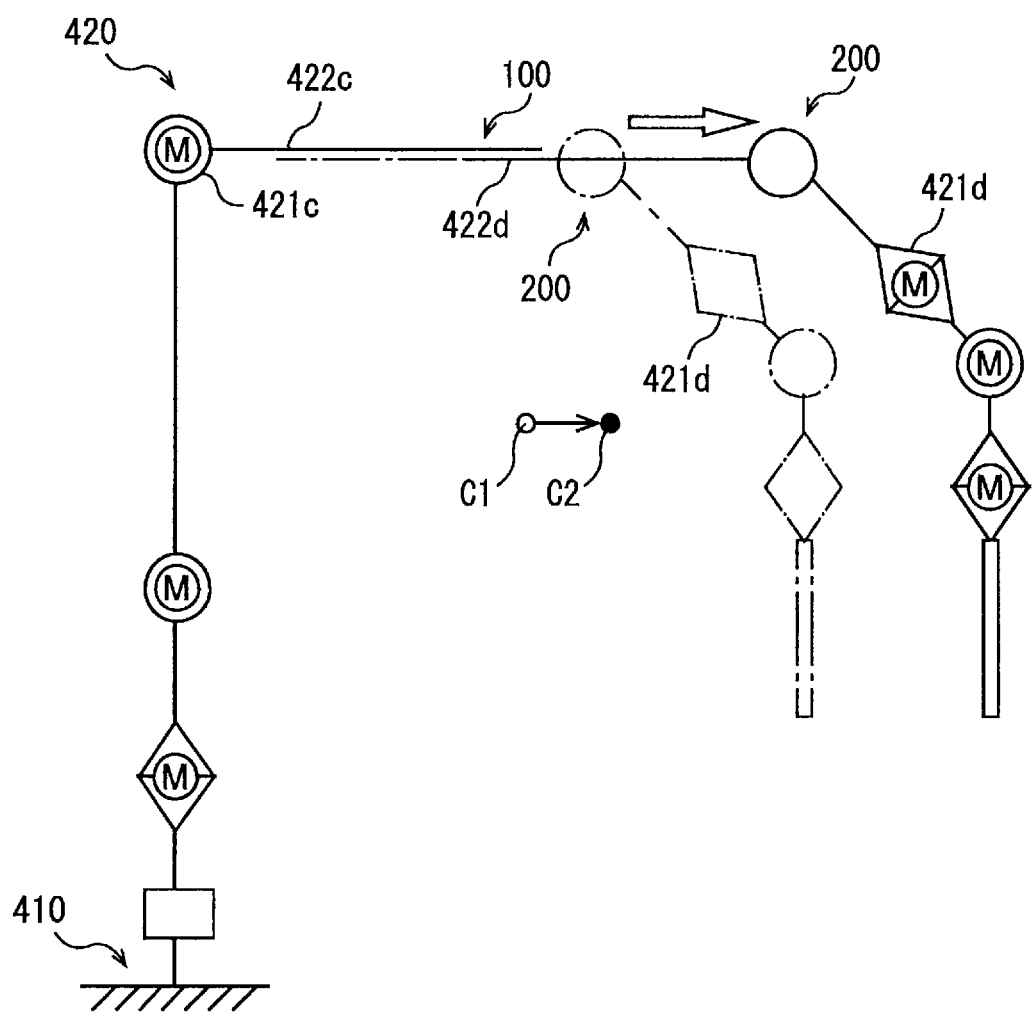

[Fig. 17]
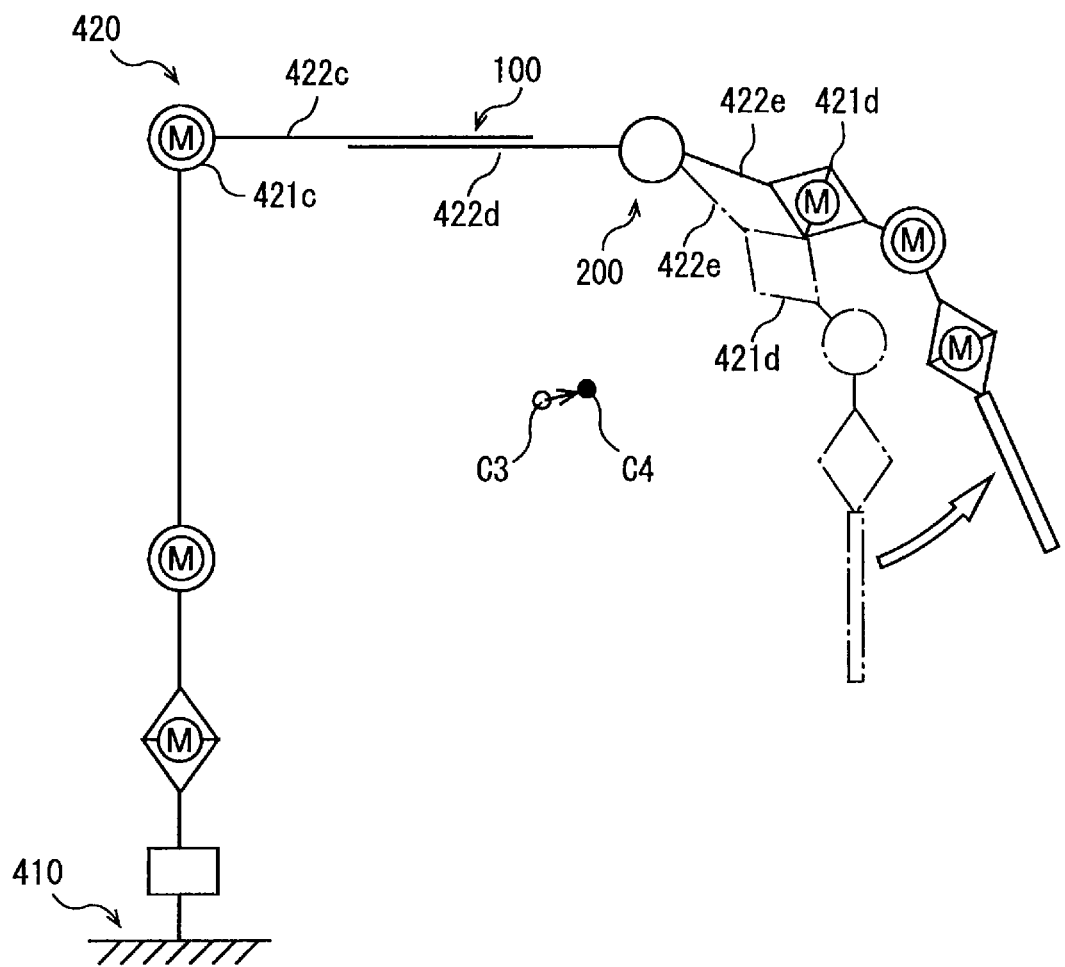

[Fig. 18]
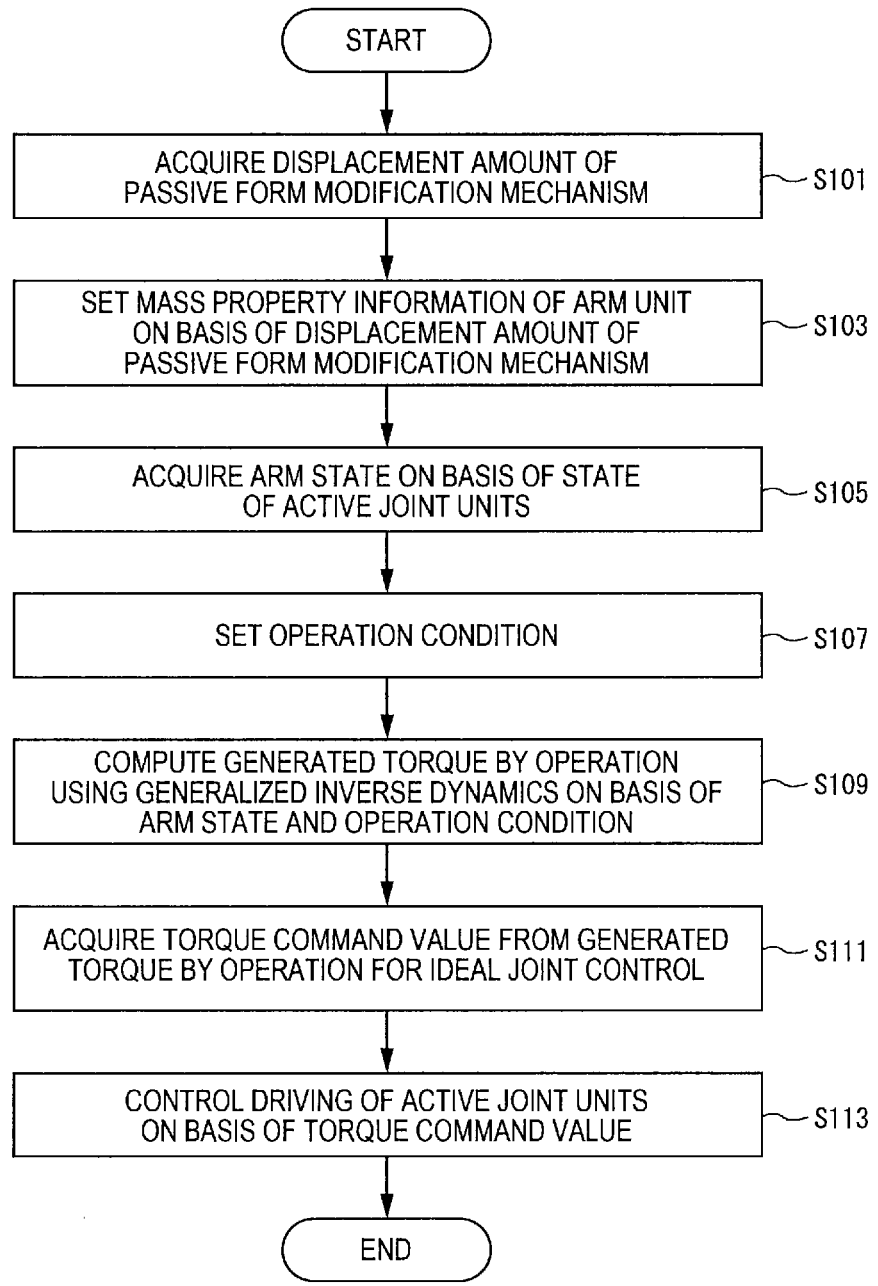

[Fig. 19]
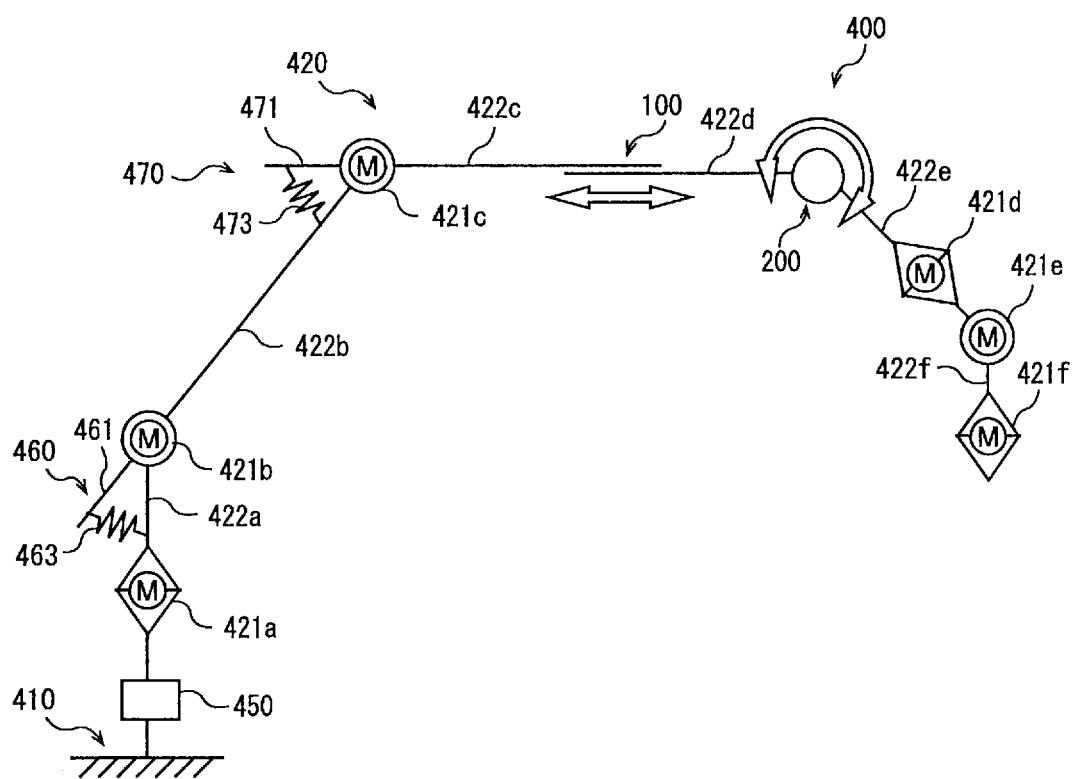

MEDICAL SUPPORT ARM APPARATUS

CROSS REFERENCE TO RELATED APPLICATIONS

This application claims the benefit of Japanese Priority Patent Application JP 2016-217751 filed Nov. 8, 2016, the entire contents of which are incorporated herein by reference.

TECHNICAL FIELD

The present disclosure relates to a medical support arm apparatus.

BACKGROUND ART

In the medical field, support arm apparatuses in which a certain medical tool is supported on the front end are being used widely to perform work more accurately and more quickly. Generally, a support arm apparatus is provided with an arm unit made up of a multi-link structure in which multiple links are joined to each other by joint units, and by controlling rotational driving in the multiple joint units, the driving of the support arm apparatus as a whole is controlled. In a medical support arm apparatus used during surgery or the like for the purpose of supporting a device such as an endoscope or microscope camera, or holding an organ, safety is demanded so that operation which is unintended by the user does not occur while the apparatus is being operated. To satisfy such demand for safety during operation, there exist medical support arm apparatuses which use force control actuators to enable execution of whole body cooperative control of the arm unit.

For example, Patent Literature 1 discloses a medical support arm apparatus in which each of multiple joint units is provided with a torque sensor for detecting the torque acting on the relevant joint unit, and which drives each actuator in accordance with the detected torque to control the operation of each joint unit. In such a medical support arm apparatus, each actuator is controlled to cancel out gravity acting on the arm unit, while in addition, actuators are controlled to assist the motion of the arm unit in the direction of a force applied additionally from outside.

CITATION LIST

Patent Literature

PTL 1: WO 2015/046081

SUMMARY

Technical Problem

With a medical support arm apparatus, there is demand for more compactness to ensure enough field of view and working space for the doctor during surgery, or so as not to impeded the arrangement of many pieces of equipment inside an operating room. However, with a medical support arm apparatus, although a more compact apparatus is demanded, the demanded degree of freedom or movable range is large, depending on the content or purpose of the surgical technique. To satisfy the demands of degree of freedom or movable range, the number of joint units in the arm unit has to be increased, or the length of each link constituting the arm unit has to be lengthened. In this way, with a medical support arm apparatus, it is desirable to satisfy the conflicting demands of a more compact apparatus, and a high degree of freedom or wide movable range.

Accordingly, the present disclosure proposes a new and improved medical support arm apparatus that moderates increased bulk of the apparatus while also enabling the realization of a high degree of freedom or a wide movable range of the arm unit.

Solution to Problem

According to an embodiment of the present disclosure, there is provided a medical support system, including a support arm having one or more active joints and one or more passive coupling mechanisms, and processing circuitry configured to obtain information indicating a change due to movement of the one or more passive coupling mechanisms and control the one or more active joints based on the obtained information indicating the change.

According to another embodiment of the present disclosure, there is provided a medical device including processing circuitry configured to obtain information indicating a change due to movement of one or more passive coupling mechanisms, and control one or more active joints based on the obtained information indicating the change.

According to another embodiment of the present disclosure, there is provided a medical image processing method, including obtaining information indicating a change due to movement of one or more passive coupling mechanisms and controlling one or more active joints based on the obtained information indicating the change.

Advantageous Effects of Invention

According to an embodiment of the present disclosure as described above, increased bulk of the apparatus can be moderated, while at the same time, a high degree of freedom or a wide movable range of the arm unit can be realized.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 is a diagram illustrating an example of a schematic configuration of an endoscopic surgery system to which a medical support arm apparatus according to an embodiment of the present disclosure is applicable.

FIG. 2 is a block diagram illustrating an example of a functional configuration of the camera head and the CCU illustrated in FIG. 1.

FIG. 3 is a perspective view illustrating an exemplary configuration of a medical support arm apparatus according to an embodiment of the present disclosure.

FIG. 4 is an explanatory diagram that schematically illustrates a medical support arm apparatus according to the embodiment.

FIG. 5 is a cross-section view illustrating an exemplary configuration of an actuator provided in an active joint unit.

FIG. 6 is an explanatory diagram illustrating an exemplary configuration of a passive slide mechanism.

FIG. 7 is an explanatory diagram of the passive slide mechanism illustrated in FIG. 6 viewed from above.

FIG. 8 is a cross-section diagram of the I-I cross-section in FIG. 6 viewed in the direction of the arrows.

FIG. 9 is a cross-section diagram of the II-II cross-section in FIG. 6 viewed in the direction of the arrows.

FIG. 10 is an explanatory diagram illustrating a state in which the slide amount of a passive slide mechanism is changed.

FIG. 11 is an explanatory diagram illustrating an exemplary configuration of a passive joint unit.

FIG. 12 is an explanatory diagram of the passive joint unit illustrated in FIG. 11 viewed from below.

FIG. 13 is a cross-section diagram of the III-III cross-section in FIG. 11 viewed in the direction of the arrows.

FIG. 14 is an explanatory diagram for explaining a detachable range of a passive joint unit.

FIG. 15 is a block diagram illustrating an exemplary configuration of a medical support arm apparatus.

FIG. 16 is an explanatory diagram illustrating a shift in the center of gravity due to a slide operation by a passive slide mechanism.

FIG. 17 is an explanatory diagram illustrating a shift in the center of gravity due to a rotation operation by a passive joint unit.

FIG. 18 is a flowchart illustrating a driving control process by a control unit.

FIG. 19 is an explanatory diagram for explaining a gravity compensation mechanism.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. Basic configuration of endoscopic surgery system
1-1. Endoscope
1-2. Various devices provided on cart
1-3. Schematic configuration of medical support arm apparatus
1-4. Light source device
1-5. Camera head and CCU
2. Specific configuration example of medical support arm apparatus
2-1. External appearance of support arm apparatus
2-2. Exemplary configuration of active joint unit
2-3. Passive form modification mechanisms
2-3-1. Passive slide mechanism
2-3-2. Passive joint unit
3. Exemplary configuration of control apparatus
3-1. Whole body cooperative control
3-1-1. Virtual force computation process
3-1-2. Actual force computation process
3-2. Ideal joint control unit
3-3. Application of mass property information of arm unit
4. Example of control method of support arm apparatus
5. Modifications
6. Conclusion

1. BASIC CONFIGURATION OF ENDOSCOPIC SURGERY SYSTEM

First, a basic configuration of an endoscopic surgery system to which a medical support arm apparatus according to an embodiment of the present disclosure (hereinafter also simply called the "support arm apparatus") is applicable will be described.

FIG. 1 is a diagram illustrating an example of a schematic configuration of an endoscopic surgery system 5000 to which a support arm apparatus according to an embodiment of the present disclosure may be applied. FIG. 1 illustrates a situation in which a surgeon (doctor) 5067 is using an endoscopic surgery system 5000 to perform surgery on a patient 5071 lying on a patient bed 5069. As illustrated in the diagram, the endoscopic surgery system 5000 is made up of an endoscope 5001, other surgical instruments 5017, a support arm apparatus 5027 that supports the endoscope 5001, and a cart 5037 on which are provided various apparatuses for endoscopic surgery.

In endoscopic surgery, instead of opening up the abdomen by cutting the abdominal wall, tubular hole-opening tools called trocars 5025a to 5025d are used to puncture the abdominal wall in multiple places. Subsequently, the lens tube 5003 of the endoscope 5001 and other surgical instruments 5017 are inserted into the body cavity of the patient 5071 from the trocars 5025a to 5025d. In the illustrated example, a pneumoperitoneum tube 5019, an energy treatment tool 5021, and forceps 5023 are inserted into the body cavity of the patient 5071 as the other surgical instruments 5017. The energy treatment tool 5021 is a treatment tool that makes incisions into and ablates tissues, or seals blood vessels or the like, with a high-frequency electric current or ultrasonic vibration. However, the surgical instruments 5017 illustrated in the diagram are merely an example, and any of various types of surgical instruments typically used in endoscopic surgery, such as tweezers and retractors, for example, may also be used as the surgical instruments 5017.

An image of the operating site inside the body cavity of the patient 5071 taken by the endoscope 5001 is displayed on a display device 5041. The surgeon 5067 uses the energy treatment tool 5021 and the forceps 5023 to perform treatments, such as excising an affected area, for example, while viewing in real-time the image of the operating site displayed on the display device 5041. Note that, although omitted from the diagram, the pneumoperitoneum tube 5019, the energy treatment tool 5021, and the forceps 5023 are supported by a person such as the surgeon 5067 or an assistant during surgery.

<1-1. Endoscope>

The endoscope 5001 is made up of a lens tube 5003 having a region of certain length from the front end that is inserted into the body cavity of the patient 5071, and a camera head 5005 connected to the base end of the lens tube 5003. In the example illustrated in the diagram, an endoscope 5001 configured as a so-called rigid scope having a rigid lens tube 5003 is illustrated, but the endoscope 5001 may also be configured as a so-called flexible scope having a flexible lens tube 5003.

On the front end of the lens tube 5003, there is provided an opening into which an objective lens is fitted. A light source device 5043 is connected to the endoscope 5001. Light generated by the light source device 5043 is guided up to the front end of the lens tube 5003 by a light guide extending inside the lens tube 5003, and is radiated through the objective lens towards an observation target inside the body cavity of the patient 5071. Note that the endoscope 5001 may be a forward-viewing scope, an oblique-viewing scope, or a side-viewing scope.

An optical system and an image sensor are provided inside the camera head 5005, and reflected light from the observation target (observation light) is condensed onto the image sensor by the optical system. Observation light is photoelectrically converted by the image sensor, and an electrical signal corresponding to the observation light, or in other words, an image signal corresponding to the observed image, is generated. The image signal is transmitted as RAW data to a camera control unit (CCU) 5039. Note that the camera head 5005 is provided with a function of adjusting the magnification and the focus distance by appropriately driving the optical system.

Note that, to support stereoscopic vision (3D display) or the like, for example, the camera head 5005 may also be provided with multiple image sensors. In this case, multiple relay optical subsystems are provided inside the lens tube 5003 to guide the observation light to each of the multiple image sensors.

<1-2. Various Devices Provided on Cart>

The CCU 5039 is made up of components such as a central processing unit (CPU) and a graphics processing unit (GPU), and centrally controls the operation of the endoscope 5001 and the display device 5041. Specifically, the CCU 5039 subjects an image signal received from the camera head 5005 to various types of image processing for displaying an image based on the image signal, such as development process (demosaicing process), for example. The CCU 5039 provides an image signal that has been subjected to such image processing to the display device 5041. Also, the CCU 5039 transmits a control signal to the camera head 5005 to control the driving thereof. The control signal may include information related to imaging parameters, such as the magnification and focus distance.

The display device 5041, under control by the CCU 5039, displays an image based on an image signal subjected to image processing by the CCU 5039. In a case in which the endoscope 5001 supports imaging at a high resolution such as 4K (3840 horizontal pixels by 2160 vertical pixels) or 8K (7680 horizontal pixels by 4320 vertical pixels), and/or supports 3D display, for example, a device compatible with each and capable of high-resolution display and/or capable of 3D display may be used as the display device 5041. In the case in which imaging at a high resolution such as 4K or 8K is supported, a device with a size of 55 inches or more may be used as the display device 5041 to thereby obtain an even deeper sense of immersion. Also, depending on the application, multiple display devices 5041 at different resolutions and sizes may also be provided.

The light source device 5043 is made up of a light source such as a light-emitting diode (LED), for example, and supplies the endoscope 5001 with irradiating light when imaging the operating site.

An arm control device 5045 is made up of a processor such as a CPU, for example, and by operating in accordance with a certain program, controls the driving of the arm unit 5031 of the support arm apparatus 5027 in accordance with a certain control method.

An input device 5047 is an input interface with respect to the endoscopic surgery system 5000. Through the input device 5047, the user is able to input various information and instructions into the endoscopic surgery system 5000. For example, through the input device 5047, the user inputs various information related to surgery, such as physical information about the patient, and information about surgical procedures. As another example, through the input device 5047, the user inputs instructions to drive the arm unit 5031, instructions to change the imaging parameters of imaging by the endoscope 5001 (such as the type of irradiating light, the magnification, and the focus distance), instructions to drive the energy treatment tool 5021, and the like.

The type of the input device 5047 is not limited, and the input device 5047 may be any of various known types of input devices. For example, devices such as a mouse, a keyboard, a touch panel, a switch, a footswitch 5057, and/or a lever may be applied as the input device 5047. In the case in which a touch panel is used as the input device 5047, the touch panel may be provided on the display screen of the display device 5041.

Alternatively, the input device 5047 is a device worn by the user, such as an eyeglasses-style wearable device or a head-mounted display (HMD), for example, and various inputs are performed in accordance with the user's gestures or gaze detected by these devices. Also, the input device 5047 includes a camera able to detect the user's movement, and various inputs are performed in accordance with the user's gestures or gaze detected from a picture imaged by the camera. Furthermore, the input device 5047 includes a microphone able to pick up the user's voice, and various inputs are performed by voice via the microphone. In this way, by configuring the input device 5047 to be capable of accepting the input of various types of information in a noncontact manner, a user belonging to a clean area in particular (for example, the surgeon 5067) becomes able to operate equipment belonging to an unclean area in a non-contact manner. Also, since the user becomes able to operate equipment without taking one's hands away from the tools the user is holding, user convenience is improved.

A treatment tool control device 5049 controls the driving of the energy treatment tool 5021 to cauterize or make incisions into tissue, seal blood vessels, or the like. The pneumoperitoneum device 5051 delivers gas into the body cavity through the pneumoperitoneum tube 5019 to inflate the body cavity of the patient 5071 for the purpose of securing a field of view for the endoscope 5001 and securing a workspace for the surgeon. The recorder 5053 is a device capable of recording various types of information related to surgery. The printer 5055 is a device capable of printing out various types of information related to surgery in various formats, such as text, images, or graphs.

<1-3. Schematic Configuration of Medical Support Arm Apparatus>

The support arm apparatus 5027 is provided with an arm unit 5031 that extends from a base unit 5029. In the illustrated example, the arm unit 5031 is made up of joint units 5033*a*, 5033*b*, and 5033*c*, as well as links 5035*a* and 5035*b*, and is driven by control commands from the arm control device 5045. The endoscope 5001 is supported by the arm unit 5031, with the position and attitude controlled thereby. With this arrangement, locking of the endoscope 5001 in a stable position may be realized.

The support arm apparatus 5027 is equipped with a base unit 5029 which acts as a base, and an arm unit 5031 which extends from the base unit 5029. In the illustrated example, the arm unit 5031 is made up of multiple joint units 5033*a*, 5033*b*, and 5033*c*, as well as multiple links 5035*a* and 5035*b* joined by the joint unit 5033*b*, but in FIG. 1, for the sake of simplicity, the configuration of the arm unit 5031 is illustrated in a simplified manner. In actuality, factors such as the shapes, numbers, and arrangement of the joint units 5033*a* to 5033*c* and the links 5035*a* and 5035*b*, and the directions of the rotation axes of the joint units 5033*a* to 5033*c* may be set appropriately so that the arm unit 5031 has the desired degrees of freedom. For example, the arm unit 5031 preferably may be configured to have six or more degrees of freedom. With this arrangement, it is possible to move the endoscope 5001 freely within the movable range of the arm unit 5031, and thus it becomes possible to insert the lens tube 5003 of the endoscope 5001 into the body cavity of the patient 5071 from a desired direction.

The joint units 5033a to 5033c are provided with an actuator, and the joint units 5033a to 5033c are configured to be rotatable about a certain rotation axis in accordance with the driving of the actuator. By controlling the driving of the actuator with the arm control device 5045, the rotational angle of each of the joint units 5033a to 5033c is controlled, and the driving of the arm unit 5031 is controlled. With this arrangement, control of the position and the attitude of the endoscope 5001 may be realized. At this point, the arm control device 5045 is able to control the driving of the arm unit 5031 with any of various known types of control methods, such as force control or position control.

For example, by having the surgeon 5067 perform appropriate operation input via the input device input device 5047 (including the footswitch 5057), the driving of the arm unit 5031 may be controlled appropriately by the arm control device 5045 in accordance with the operation input, and the position and the attitude of the endoscope 5001 may be controlled. By such control, after moving the endoscope 5001 on the front end of the arm unit 5031 from an arbitrary position to an arbitrary position, the endoscope 5001 can be supported securely at the new position. Note that the arm unit 5031 may also be operated by what is called a master-slave method. In this case, the arm unit 5031 may be operated remotely by a user via the input device 5047 installed in a location distant from the operating room.

Also, in a case in which force control is applied, the arm control device 5045 may receive external force from the user, and drive the actuator of each of the joint units 5033a to 5033c so that the arm unit 5031 moves smoothly in response to the external force, also known as power assist control. With this arrangement, when the user moves the arm unit 5031 while touching the arm unit 5031 directly, the arm unit 5031 can be moved with comparatively light force. Consequently, it becomes possible to move the endoscope 5001 more intuitively with a simpler operation, and user convenience can be improved.

Herein, in endoscopic surgery, typically the endoscope 5001 has been supported by a doctor called a scopist. In contrast, by using the support arm apparatus 5027, it becomes possible to keep the position of the endoscope 5001 fixed more reliably without manual work, and thus image of the operating site can be obtained consistently, making it possible to perform surgery smoothly.

Note that the arm control device 5045 does not necessarily have to be provided on the cart 5037. Also, the arm control device 5045 does not necessarily have to be a single device. For example, the arm control device 5045 may also be proved respectively in each of the joint units 5033a to 5033c of the arm unit 5031 of the support arm apparatus 5027, and the multiple arm control devices 5045 may cooperate with each other to realize driving control of the arm unit 5031.

<1-4. Light Source Device>

The light source device 5043 supplies the endoscope 5001 with irradiating light when imaging the operating site. The light source device 5043 is made up of a white light source configured by an LED, a laser light source, or a combination of the two, for example. At this point, in the case in which the white light source is configured by a combination of RGB laser light sources, the output intensity and output timing of each color (each wavelength) can be controlled with high precision, and thus the white balance of the captured image can be adjusted with the light source device 5043. Also, in this case, by irradiating the observation target with laser light from each of the RGB laser light sources in a time-division manner, and controlling the driving of the image sensor of the camera head 5005 in synchronization with the irradiation timings, it is also possible to capture images corresponding to R, G, and B, respectively, in a time-division manner. According to such a method, color images can be obtained without providing the image sensor with a color filter.

Also, the driving of the light source device 5043 may also be controlled so as to change the intensity of the light to output every time a certain amount of time elapses. By controlling the driving of the image sensor of the camera head 5005 in synchronization with the timings of changing the light intensity to acquire images in a time-division manner, and compositing the images together, it is possible to generate a high dynamic range image without what are called crushed blacks and blown-out whites.

Additionally, the light source device 5043 may also be configured to be able to supply light in a certain wavelength band corresponding to special imaging. With special imaging, for example, the wavelength dependency of light absorption by tissues of the body is utilized, and light is radiated in a narrow band compared to the irradiating light during normal observation (that is, white light) to thereby image certain tissues, such as blood vessels in the superficial portion of the mucous membrane, at a high contrast, also known as narrow band imaging (NBI). Alternatively, with special imaging, fluorescent observation that obtains an image with fluorescent light by radiating excitation light may also be conducted. With fluorescent observation, it is possible to irradiate a body tissue with excitation light and observe fluorescent light from the body tissue (autofluorescence observation), or locally inject a reagent such as indocyanine green (ICG) into a body tissue while also irradiating that body tissue with excitation light corresponding to the fluorescence wavelength of the reagent to obtain a fluorescent image, or the like. The light source device 5043 may be configured to be able to supply narrow-band light and/or excitation light corresponding to such special imaging.

<1-5. Camera Head and CCU>

The functions of the camera head 5005 and the CCU 5039 of the endoscope 5001 will be described in further detail with reference to FIG. 2. FIG. 2 is a block diagram illustrating an example of a functional configuration of the camera head 5005 and the CCU 5039 illustrated in FIG. 1.

Referring to FIG. 2, functionally, the camera head 5005 includes a lens unit 5007, an imaging unit 5009, a driving unit 5011, a communication unit 5013, and a camera head control unit 5015. Also, functionally, the CCU 5039 includes a communication unit 5059, an image processing unit 5061, and a control unit 5063. The camera head 5005 and the CCU 5039 are bidirectionally communicably connected by a transmission cable 5065.

First, a functional configuration of the camera head 5005 will be described. The lens unit 5007 is an optical system provided in the part that connects to the lens tube 5003. Observation light taken in from the front end of the lens tube 5003 is guided up to the camera head 5005, and is incident on the lens unit 5007. The lens unit 5007 is made up of a combination of multiple lenses, including a zoom lens and a focus lens. The optical characteristics of the lens unit 5007 are adjusted to condense observation light onto the photosensitive face of an image sensor in the imaging unit 5009. Also, the zoom lens and the focus lens are configured to be able to move position on the optical axis to adjust the magnification and the focus of the captured image.

The imaging unit 5009 is made up of an image sensor, and is disposed downstream from the lens unit 5007. Observation light passing through the lens unit 5007 is condensed onto the photosensitive face of the image sensor, and by photoelectric conversion, an image signal corresponding to the observed image is generated. The image signal generated by the imaging unit 5009 is provided to the communication unit 5013.

For the image sensor constituting the imaging unit 5009, a complementary metal-oxide semiconductor (CMOS) type image sensor having a Bayer array to enable color imaging is used, for example. Note that a sensor capable of capturing high-resolution images of 4K or greater may be used as the image sensor, for example. By obtaining a high-resolution image of the operating site, the surgeon 5067 becomes able to grasp the state of the operating site in greater detail, and proceed with surgery more smoothly.

Also, the image sensor constituting the imaging unit 5009 includes a pair of image sensors for respectively acquiring image signals for the right eye and the left eye corresponding to 3D display. By presenting a 3D display, the surgeon 5067 becomes able to grasp the depth of biological tissue at the operating site more accurately. Note that if the imaging unit 5009 has a multi-chip configuration, the lens unit 5007 likewise is provided with multiple subsystems corresponding to each of the image sensors.

Also, the imaging unit 5009 is not necessarily provided in the camera head 5005. For example, the imaging unit 5009 may also be provided inside the lens tube 5003, directly behind the objective lens.

The driving unit 5011 is made up of actuators, and under control from the camera head control unit 5015, moves the zoom lens and the focus lens of the lens unit 5007 by a certain distance along the optical axis. With this arrangement, the magnification and the focus of the image captured by the imaging unit 5009 may be adjusted appropriately.

The communication unit 5013 is made up of a communication device for transmitting and receiving various information to and from the CCU 5039. The communication unit 5013 transmits an image signal obtained from the imaging unit 5009 as RAW data to the CCU 5039 through the transmission cable 5065. At this point, to display the captured image of the operating site with low latency, the image signal preferably is transmitted by optical communication. This is because during surgery, the surgeon 5067 performs surgery while observing the state of the affected area via the captured image, and thus for safer and more reliable surgery, there is demand for the moving image of the operating site to be displayed as close to real-time as possible. In the case in which optical communication is conducted, the communication unit 5013 is provided with a photoelectric conversion module that converts an electrical signal into an optical signal. The image signal is converted into an optical signal by the photoelectric conversion module, and then transmitted to the CCU 5039 through the transmission cable 5065.

Also, the communication unit 5013 receives from the CCU 5039 a control signal for controlling the driving of the camera head 5005. The control signal includes information related to imaging parameters, such as information specifying the frame rate of the captured image, information specifying the exposure value during imaging, and/or information specifying the magnification and focus of the captured image, for example. The communication unit 5013 provides the received control signal to the camera head control unit 5015. Note that the control signal from the CCU 5039 may also be transmitted by optical communication. In this case, the communication unit 5013 is provided with a photoelectric conversion module that converts an optical signal into an electrical signal, whereby the control signal is converted into an electrical signal by the photoelectric conversion module, and then provided to the camera head control unit 5015.

Note that the above imaging parameters such as the frame rate, the exposure value, the magnification, and the focus are set automatically by the control unit 5063 of the CCU 5039 on the basis of the acquired image signal. In other words, what are called an auto exposure (AE) function, an auto focus (AF) function, and an auto white balance (AWB) function are provided in the endoscope 5001.

The camera head control unit 5015 controls the driving of the camera head 5005 on the basis of a control signal from the CCU 5039 received via the communication unit 5013. For example, the camera head control unit 5015 controls the driving of the image sensor of the imaging unit 5009, on the basis of information specifying the frame rate of the captured image and/or information specifying the exposure during imaging. As another example, the camera head control unit 5015 appropriately moves the zoom lens and the focus lens of the lens unit 5007 via the driving unit 5011, on the basis of information specifying the magnification and the focus of the captured image. Additionally, the camera head control unit 5015 may also be provided with a function of storing information for identifying the lens tube 5003 and the camera head 5005.

Note that by disposing parts of the configuration, such as the lens unit 5007 and the imaging unit 5009, inside a highly airtight and waterproof sealed structure, the camera head 5005 can be made to withstand an autoclaving sterilization process.

Next, a functional configuration of the CCU 5039 will be described. The communication unit 5059 is made up of a communication device for transmitting and receiving various information to and from the camera head 5005. The communication unit 5059 receives an image signal transmitted from the camera head 5005 through the transmission cable 5065. At this point, as described earlier, the image signal preferably may be transmitted by optical communication. In this case, to support optical communication, the communication unit 5059 is provided with a photoelectric conversion module that converts an optical signal into an electrical signal. The communication unit 5059 provides the image signal converted into an electrical signal to the image processing unit 5061.

Also, the communication unit 5059 transmits a control signal for controlling the driving of the camera head 5005 to the camera head 5005. The control signal may also be transmitted by optical communication.

The image processing unit 5061 performs various types of image processing on the image signal made of RAW data transmitted from the camera head 5005. The image processing includes various types of established signal processing, such as a development process, an image quality-improving process (such as a band enhancement process, a super-resolution process, a noise reduction (NR) process, and/or a shake correction process), and/or an enlargement process (digital zoom process), for example. Also, the image processing unit 5061 conducts a wave detection process on the image signal to conduct AE, AF, and AWB.

The image processing unit 5061 is made of a processor such as a CPU or GPU, and by having the processor operate in accordance with a certain program, the image processing and wave detection process described above may be conducted. Note that in the case in which the image processing unit 5061 is made up of multiple GPUs, the image processing unit 5061 appropriately divides up information related to the image signal, and conducts image processing in parallel with the multiple GPUs.

The control unit 5063 performs various controls related to the imaging of the operating site by the endoscope 5001 and the display of a captured image therefrom. For example, the control unit 5063 generates a control signal for controlling the driving of the camera head 5005. At this point, in a case in which imaging parameters are input by the user, the control unit 5063 generates a control signal on the basis of the input by the user. Alternatively, in a case in which the endoscope 5001 is provided with an AE function, an AF function, and an AWB function, the control unit 5063 appropriately computes an optimal exposure value, focus distance, and white balance in accordance with the results of the wave detection process by the image processing unit 5061, and generates a control signal.

In addition, the control unit 5063 causes the display device 5041 to display an image of the operating site on the basis of the image signal subjected to image processing by the image processing unit 5061. At this point, the control unit 5063 uses any of various types of image recognition technology to recognize various objects in the operating site image. For example, by detecting features such as the edge shapes and colors of objects included in the operating site image, the control unit 5063 is able to recognize surgical instruments such as forceps, a specific site of the body, hemorrhaging, mist during usage of the energy treatment tool 5021, and the like. When causing the display device 5041 to display an image of the operating site, the control unit 5063 uses the recognition results to overlay various surgical assistance information onto the image of the operating site. By overlaying and providing the surgeon 5067 with surgical assistance information, it becomes possible to proceed with surgery more safely and reliably.

The transmission cable 5065 that connects the camera head 5005 and the CCU 5039 is an electrical signal cable supporting the communication of electrical signals, optical fiber supporting optical communication, or a composite cable of the above.

At this point, in the illustrated example, communication is conducted in a wired manner using the transmission cable 5065, but communication between the camera head 5005 and the CCU 5039 may also be conducted wirelessly. In the case in which the communication between the two is conducted wirelessly, it is no longer necessary to lay down the transmission cable 5065 inside the operating room, and thus a situation in which the movement of medical staff inside the operating room is impeded by the transmission cable 5065 may be resolved.

The above thus describes an example of an endoscopic surgery system 5000 to which a medical support arm apparatus according to an embodiment of the present disclosure may be applied. Note that herein, although an endoscopic surgery system 5000 is described as an example, the system to which technology according to an embodiment of the present disclosure may be applied is not limited to such an example. For example, a medical support arm apparatus according to an embodiment of the present disclosure may also be applied to a flexible endoscopic system used for examinations, or a microscopic surgical system.

2. SPECIFIC CONFIGURATION EXAMPLE OF MEDICAL SUPPORT ARM APPARATUS

Next, a specific configuration example of a medical support arm apparatus according to an embodiment of the present disclosure will be described in detail. The support arm apparatus described hereinafter is an example configured as a support arm apparatus that supports an endoscope on the front end of an arm unit, but the present embodiment is not limited to such an example.

<2-1. External Appearance of Support Arm Apparatus>

First, a schematic configuration of a support arm apparatus 400 according to the present embodiment will be described with reference to FIG. 3. FIG. 3 is a schematic diagram illustrating the external appearance of a support arm apparatus 400 according to the present embodiment.

The support arm apparatus 400 according to the present embodiment is provided with a base unit 410 and an arm unit 420. The base unit 410 is the base of the support arm apparatus 400, and the arm unit 420 extends from the base unit 410. Also, although not illustrated in FIG. 3, a control unit that centrally controls the support arm apparatus 400 may also be provided inside the base unit 410, and the driving of the arm unit 420 may be controlled by the control unit. The control unit is made up of any of various types of signal processing circuits, such as a CPU or a DSP, for example.

The arm unit 420 includes multiple active joint units 421a to 421f, multiple links 422a to 422f, and an endoscopic device 423 acting as a front end unit provided on the front end of the arm unit 420.

The links 422a to 422f are approximately rod-shaped members. One end of the link 422a is joined to the base unit 410 via the active joint unit 421a, while the other end of the link 422a is joined to one end of the link 422b via the active joint unit 421b, and additionally, the other end of the link 422b is joined to one end of the link 422c via the active joint unit 421c. The other end of the link 422 is joined to the link 422d via a passive slide mechanism 100, and additionally, the other end of the link 422d is joined to one end of the link 422e via a passive joint unit 200. The other end of the link 422e is joined to one end of the link 422f via the active joint units 421d and 421e. The endoscopic device 423 is joined to the front end of the arm unit 420, or in other words the other end of the link 422f, via the active joint unit 421f. In this way, the base unit 410 acts as a fulcrum, and the ends of the multiple links 422a to 422f are joined to each other by the active joint units 421a to 421f, the passive slide mechanism 100, and the passive joint unit 200, thereby constituting an arm shape extending from the base unit 410.

By controlling the driving of an actuator provided in each of the active joint units 421a to 421f of such an arm unit 420, the position and the attitude of the endoscopic device 423 is controlled. In the present embodiment, the front end of the endoscopic device 423 enters into a patient's body cavity which is the operating site, and images a partial region of the operating site. However, the front end unit provided on the front end of the arm unit 420 is not limited to the endoscopic device 423, and any of various types of medical tools may be connected to the front end of the arm unit 420 as the front end unit. In this way, the support arm apparatus 400 according to an embodiment of the present disclosure is configured as a medical support arm apparatus provided with a medical tool.

At this point, in the following, the support arm apparatus 400 will be described by defining coordinate axes as illustrated in FIG. 3. Also, an up-and-down direction, a forwardand-back direction, and a right-and-left direction are defined to match the coordinate axes. Namely, the up-and-down direction with respect to the base unit 410 installed on the floor is defined to be the z-axis direction and the up-and-down direction. Also, the direction which is orthogonal to the z-axis, and in which the arm unit 420 extends from the base unit 410 (in other words, the direction in which the endoscopic device 423 is positioned with respect to the base unit 410) is defined to be the y-axis direction and the forward-and-back direction. Additionally, the direction that is orthogonal to the y-axis and the z-axis is defined to be the x-axis direction and the left-and-right direction.

The active joint units 421a to 421f rotatably join the links to each other. Each of the active joint units 421a to 421f includes an actuator, and includes a rotation mechanism that is rotationally driven about a certain rotation axis by the driving of the actuator. By respectively controlling the rotational driving in each of the active joint units 421a to 421f, driving of the arm unit 420 can be controlled so as to extend or contract (fold up) the arm unit 420, for example. Herein, the driving of the active joint units 421a to 421f may be controlled by known whole body cooperative control and ideal joint control, for example. As described above, since the active joint units 421a to 421f include a rotating mechanism, in the following description, driving control of the active joint units 421a to 421f specifically means that the rotational angle and/or the generated torque of the active joint units 421a to 421f (the torque generated by the active joint units 421a to 421o are controlled.

The passive slide mechanism 100 is one mode of a passive form modification mechanism, and joins the link 422c and the link 422d so as to allow the links to advance towards or retreat from each other in a certain direction. For example, the passive slide mechanism 100 may join the link 422c and the link 422d so as to allow linear motion with respect to each other. However, the advancing or retreating movement of the link 422c and the link 422d is not limited to linear movement, and may also be advancing or retreating movement in a direction that forms an arc. An operation of advancing or retreating motion is performed on the passive slide mechanism 100 by the user, for example, thereby varying the distance between the active joint unit 421c on the one end of the link 422c, and the passive joint unit 200. With this arrangement, the overall form of the arm unit 420 may be changed. The configuration of the passive slide mechanism 100 will be described in detail later.

The passive joint unit 200 is one mode of a passive form modification mechanism, and joins the link 422d and the link 422e so as to allow the links to rotate with respect to each other. An operation of rotational movement is performed on the passive joint unit 200 by the user, for example, thereby varying the angle obtained between the link 422d and the link 422e. With this arrangement, the overall form of the arm unit 420 may be changed. The configuration of the passive joint unit 200 will be described in detail later.

Note that in this specification, the "attitude of the arm unit" refers to a state of the arm unit in which the distances between neighboring active joint units with one or multiple links interposed are fixed, and which may change due to driving control of the actuators provided in the active joint units 421a to 421f by the control unit. Meanwhile, the "form of the arm unit" refers to a state of the arm unit which may change in response to operations performed on passive form modification mechanisms to thereby change the distances between neighboring active joint units with links interposed, or change the angle obtained between the links that join neighboring active joint units.

The support arm apparatus 400 according to the present embodiment includes six active joint units 421a to 421f, and six degrees of freedom are realized with respect to the driving of the arm unit 420. In other words, whereas driving control of the support arm apparatus 400 is realized by the driving control of the six active joint units 421a to 421f by the control unit, the passive slide mechanism 100 and the passive joint unit 200 are not subject to driving control by the control unit.

Specifically, as illustrated in FIG. 3, the active joint units 421a, 421d, and 421f are provided to make the longitudinal directions of the respectively connected links 422a and 422e and the imaging direction of the connected endoscopic device 423 into rotation axis directions. The active joint units 421b, 421c, and 421e are provided to make the x-axis direction into a rotation axis direction, the x-axis direction being the direction about which the joining angles of the respectively connected links 422a to 422c, 422e, and 422f as well as the endoscopic device 423 are changed in the y-z plane (the plane defined by the y-axis and the z-axis). In this way, in the present embodiment, the active joint units 421a, 421d, and 421f have a function of performing what is called yawing, while the active joint units 421b, 421c, and 421e have a function of performing what is called pitching.

By having such a configuration of the arm unit 420, six degrees of freedom are realized with respect to the driving of the arm unit 420 in the support arm apparatus 400 according to the present embodiment, and thus the endoscopic device 423 can be moved freely within the movable range of the arm unit 420. In FIG. 3, a hemisphere is illustrated as one example of the movable range of the endoscopic device 423. Provided that the hemisphere center point RCM (remote center of motion) is the imaging center of the operating site imaged by the endoscopic device 423, by causing the endoscopic device 423 to move over the hemispherical surface of the hemisphere in a state in which the imaging center of the endoscopic device 423 is locked to the hemisphere center point, the operating site can be imaged from a variety of angles.

FIG. 4 is a schematic diagram illustrating a configuration of the support arm apparatus 400 according to the present embodiment. The arm unit 420 of the support arm apparatus 400 is joined to the base unit 410 on the root side, and extends towards the front end side on which an endoscopic device (not illustrated) is supported. The three active joint units 421d, 421e, and 421f disposed on the front end side mainly have a function of securing operation with three degrees of freedom for the endoscopic device, and varying the imaging direction. Meanwhile, the three active joint units 421a, 421b, and 421c disposed on the root side mainly have a function of varying the position of the endoscopic device. In other words, in the support arm apparatus 400 according to the present embodiment, the rough position of the endoscopic device supported on the front end side is decided by the rotational driving of the active joint units 421a, 421b, and 421c on the root side, while at the same time, the imaging direction of the endoscopic device is decided by the rotational driving of the active joint units 421d, 421e, and 421f on the front end side.

Additionally, the root part of the 420 of the support arm apparatus 400, for example, the joining part between the link 422a and the base unit 410, may also be provided with an attitude sensor 450 for detecting the inclination of the arm unit 420 as a whole with respect to the horizontal direction. The inclination of the arm unit 420 as a whole detected by the attitude sensor 450 is used to compute the gravitational force acting on the arm unit 420, and the control unit is able to use the computed gravitational force to execute control for canceling out gravity (hereinafter also called "gravity compensation control"). For such an attitude sensor 450, a sensor using at least one of a gyro sensor and an acceleration sensor may be applied, for example.

The passive slide mechanism 100 and the passive joint unit 200 which act as passive form modification mechanisms are provided between the active joint unit 421c and the active joint unit 421d. In other words, the passive form modification mechanisms are disposed farther towards the root side than at least the three active joint units 421d to 421f disposed on the front end side of the arm unit 420. For this reason, the passive slide mechanism 100 and the passive joint unit 200 are able to change the movable range of the arm unit 420 without exerting great influence on the control of the imaging direction of the endoscopic device by the three active joint units 421d to 421f on the front end side. However, the placement positions of the passive modification mechanisms are not limited to the above example. No matter which positions the passive form modification mechanisms are disposed at, the form of the arm unit 420 can be changed.

At this point, in a case in which passive form modification mechanisms are not provided, if the degrees of freedom of the arm unit 420 (the number of active joint units) and the length of each link in the arm unit 420 are designed to accommodate the maximum movable range anticipated for the endoscopic device, the arm unit 420 itself becomes excessively large for surgical techniques in which few degrees of freedom or a small movable range is sufficient. As a result, the arm unit 420 may cause the surgeon's field of view and working space to become obstructed, or impede the arrangement of other equipment inside the operating room. Also, if the degrees of freedom of the arm unit 420 increase, the number of actuators also increases, which may cause an increase in costs and the weight of the arm unit 420. Furthermore, by lengthening the length of each link, the output demanded of the actuator provided in the active joint unit 421a on the root side increases, which may cause an increase in costs.

In contrast, the support arm apparatus 400 according to the present embodiment includes the passive slide mechanism 100 and the passive joint unit 200, and thus is able to change at least one of the distance between some of the active joint units of the arm unit 420 and the angle between some of the links. For this reason, with the support arm apparatus 400, the form of the arm unit 420 can be changed in accordance with the purpose and content of the surgical technique, and an appropriate movable range can be secured. Consequently, it is possible to keep the surgeon's field of view and working space from being obstructed more than necessary, and to keep the arrangement of other equipment inside the operating room from being impeded more than necessary. Also, with the support arm apparatus 400, it is possible to moderate cost increases in order to secure an appropriate movable range, without increasing the degrees of freedom (the number of active joint units) more than necessary.

<2-2. Exemplary Configuration of Active Joint Unit>

At this point, the configuration of the active joint units 421a to 421f will be described briefly with reference to FIG. 5. Note that herein, of the configuration of the active joint units 421a to 421f, the configuration of the actuator 430, which is the part of the configuration that mainly relates to the rotational driving of the active joint units 421a to 421f, will be described. The active joint units 421a to 421f include various configurations necessary for driving the arm unit 420, such as support members for connecting or supporting the links 422a to 422f and the endoscopic device 423. In the description thus far and in the description hereinafter, the driving of the joint units of the arm unit 420 may also mean the driving of the actuator 430 in the active joint units 421a to 421f.

FIG. 5 is a cross-section view illustrating an exemplary configuration of the actuator 430 provided in the active joint units 421a to 421f. FIG. 5 illustrates a cross-section view of the actuator 430 according to the present embodiment in the case of cutting on a plane that goes through the rotation axis.

Referring to FIG. 5, the actuator 430 is made up of a motor 424, a motor driver 425, a reduction gear 426, an encoder 427, and a torque sensor 428. The actuator 430 is an actuator corresponding to force control, for example. In the actuator 430, the rotation of the motor 424 is reduced by the reduction gear 426 at a certain reduction ratio, and transmitted to other downstream members via an output shaft. As a result, the other members are driven.

The motor 424 is a driving mechanism that produces rotational driving force. The motor 424, under control from the motor driver 425, is driven to generate torque corresponding to a torque command value from the control unit. For the motor 424, a brushless motor is used, for example. However, the present embodiment is not limited to such an example, and any of various known types of motors may be used as the motor 424.

The motor driver 425 is a driver circuit (driver integrated circuit (IC)) that rotationally drives the motor 424 by supplying current to the motor 424, and is able to control the rotation rate of the motor 424 by adjusting the amount of current supplied to the motor 424. The motor driver 425 drives the motor 424 by supplying the motor 424 with a current corresponding to a torque command value T from the control unit.

Additionally, the motor driver 425 is able to adjust a viscous drag coefficient on rotary motion of the actuator 430 by adjusting the amount of current supplied to the motor 424. With this arrangement, it becomes possible to impose a certain drag on rotary motion in the actuator 430, or in other words, on rotary motion in the active joint units 421a to 421f. For example, the active joint units 421a to 421f can be put into a state of easily rotating in response to a force imparted from the outside (in other words, a state in which the arm unit 420 is easy to move by hand), or conversely, can be put into a state of hardly rotating in response to a force imparted from the outside (in other words, a state in which the arm unit 420 is hard to move by hand).

The reduction gear 426 is joined to the rotating shaft (drive shaft) of the motor 424. The reduction gear 426 reduces by a certain reduction ratio the rotational velocity of the rotating shaft of the joined motor 424 (in other words, the rotational velocity of the input shaft), and transmits to the output shaft. In the present embodiment, the configuration of the reduction gear 426 is not limited to a specific configuration, and any of various known types of reduction gears may be used as the reduction gear 426. However, for the reduction gear 426, it is preferable to use one capable of accurately setting the reduction ratio, such as a Harmonic Drive (registered trademark), for example. In addition, the reduction ratio of the reduction gear 426 may be set appropriately according to the application of the actuator 430. For example, in the case of applying the actuator 430 to the active joint units 421a to 421f of the support arm apparatus 400 as in the present embodiment, a reduction gear 426 having a reduction ratio of approximately 1:100 may be used favorably.

The encoder 427 detects the rotational angle of the input shaft (that is, the rotational angle of the rotating shaft of the motor 424). On the basis of the rotation rate of the input shaft detected by the encoder 427, and the reduction ratio of the reduction gear 426, information such as the rotational angle, the rotational angular velocity, and the rotational angular acceleration of the active joint units 421$a$ to 421$f$ may be obtained. For the encoder 427, any of various known types of rotary encoders, such as a magnetic encoder or an optical encoder, for example, may be used. Note that in the illustrated example, the encoder 427 is provided only on the input shaft of the actuator 430, but an encoder for detecting the rotational angle, or the like, of the output shaft of the actuator 430 additionally may be provided farther downstream than the reduction gear 426.

The torque sensor 428 is connected to the output shaft of the actuator 430, and detects the torque acting on the actuator 430. The torque sensor 428 detects the torque output by the actuator 430 (generated torque). Additionally, the torque sensor 428 is also able to detect external torque imparted to the actuator 430 from the outside.

The above thus describes a configuration of the actuator 430 provided in the active joint units 421$a$ to 421$f$ with reference to FIG. 5. Herein, in the present embodiment, the behavior of the arm unit 420 is controlled by force control. With such force control, in the support arm apparatus 400, the rotational angle of each of the active joint units 421$a$ to 421$f$ and the torque acting on each of the active joint units 421$a$ to 421$f$ are detected respectively by the encoder 427 and the torque sensor 428 provided in each actuator 430. At this point, the torque acting on each of the active joint units 421$a$ to 421$f$ detected by the torque sensor 428 may also include force acting on the arm unit 420 and/or the endoscopic device 423.

In addition, onto the rotational angles detected by the encoder 427 and the torque values detected by the torque sensor 428, the current state of the arm unit 420 (such as the position and velocity) may be acquired. In the support arm apparatus 400, on the basis of the acquired state of the arm unit 420 (arm state), the torque to be generated by the actuator 430 provided in each of the active joint units 421$a$ to 421$f$ necessary for the arm unit 420 to execute a desired purpose of motion is computed, and this torque is used as a control value to drive the actuator 430 in each of the active joint units 421$a$ to 421$f$.

Note that the configuration illustrated in FIG. 5 merely illustrates one exemplary configuration of the actuator 430, and the present embodiment is not limited to such an example. For the actuator 430, it is possible to use any of various known types of actuators typically used in various devices whose behavior is controlled by force control. For example, the configurations described in previous patents by the applicant, such as JP 2009-269102A and JP 2011-209099A, may also be used favorably as the actuator 430.

In the support arm apparatus 400 according to the present embodiment, the configuration of the actuator 430 and each component constituting the actuator is not limited to the configuration described above, and may also be another configuration.

<2-3. Passive Form Modification Mechanisms>

Next, exemplary configurations of passive form modification mechanisms will be described. As described above, a passive form modification mechanism is able to change the form of the arm unit 420 by altering the distance between active joint units, or by altering the angle obtained between links, for example. With this arrangement, the movable range of the arm unit 420 may be secured in accordance with the purpose and content of the surgical technique. Hereinafter, exemplary configurations of the passive slide mechanism 100 and the passive joint unit 200 will be described as examples of passive form modification mechanisms, with reference to the drawings as appropriate.

(2-3-1. Passive Slide Mechanism)

FIGS. 6 to 9 are explanatory diagrams illustrating an exemplary configuration of a passive slide mechanism. FIG. 6 is a side view of the passive slide mechanism 100 as viewed from a direction orthogonal to the longitudinal direction of the links 422$c$ and 422$d$. FIG. 7 is a diagram of the passive slide mechanism 100 illustrated in FIG. 6 viewed from above. FIG. 8 is a diagram of the I-I cross-section of the passive slide mechanism 100 illustrated in FIG. 6 viewed in the direction of the arrows, while FIG. 9 is a diagram of the II-II cross-section of the passive slide mechanism 100 illustrated in FIG. 6 viewed in the direction of the arrows.

The passive slide mechanism 100 of the support arm apparatus 400 according to the present embodiment joins the two links 422$c$ and 422$d$ disposed between the two active joint units 421$c$ and 421$d$ so as to allow the links to advance towards or retreat from each other. In both the link 422$c$ and the link 422$d$, the shape of the cross-section orthogonal to the longitudinal direction forms an approximate U-shape (see FIG. 9). The width of one link 422$c$ is greater than the width of the other link 422$d$, allowing the other link 442$d$ to be disposed inside the one link 422$c$ having a cross-sectional U-shape. The inner face on the bottom part of the one link 422$c$ having a cross-sectional U-shape is provided with a rail part 110 in the longitudinal direction of the link 422$c$. For example, the rail part 110 may be secured to the link 422$c$ by using boss parts 111 formed in the bottom part of the link 422$c$ and fixing bolts 113, or may be formed integrally with the link 422$c$.

The outer face on the bottom part of the other link 422$d$ having a cross-sectional U-shape is provided with a slider 120. The slider 120 has a groove part 121 running in the longitudinal direction of the link 422$d$. The groove part 121 slidably fits into the rail part 110 provided on the one link 422$c$. The rail part 110 provided on the one link 422$c$ and the groove part 121 of the slider 120 provided on the other link 422$d$ have corresponding concave and convex shapes on the face extending in the depth direction of the respective cross-sectional U-shapes. For example, the groove part 121 of the slider 120 may slide and fit in from the end of the rail part 110 along the extension direction of the rail part 110. With this arrangement, a mechanism allowing the two links 422$b$ and 422$c$ to be attached and removed is formed. Also, in the state in which the slider 120 is fitted into the rail part 110, the slider 120 does not readily disengage from the rail part 110.

The slider 120 may be secured to the link 422$d$ by using fixing bolts 125, or may be formed integrally with the link 422$d$. The slider 120 may be provided on the end of the other link 422$d$, for example. By having the slider 120 move in the extension direction of the rail part 110 while the groove part 121 is guided by the rail part 110, relative linear motion of the one link 422$c$ and the other link 422$d$ becomes possible.

In the present embodiment, the passive slide mechanism 100 is able to lock the position of the one link 422$c$ and the other link 422$d$ in multiple stages. In other words, the passive slide mechanism 100 allows the two links 422$c$ and 422$d$ to slide by a slide amount (displacement amount) preset in multiple stages. For example, of the ends of the one link 422c, one side face part of the cross-sectional U-shape is provided with a positioning pin 130 and a fixing screw 140. The tips of the positioning pin 130 and the fixing screw 140 are able to penetrate the side face part of the link 422c and advance into the cross-sectional U-shape. Also, on one side face part of the cross-sectional U-shape of the other link 422d, which may oppose the side face part provided with the positioning pin 130 and the fixing screw 140 on the one link 422c, there are provided multiple positioning holes 131a, 131b, and so on that accept the tip of the positioning pin 130, and multiple indentations not illustrated that accept the tip of the fixing screw 140.

The user sets the total length of the two links 422c and 422d by inserting the tip of the positioning pin 130 into a selected one of the positioning holes 131a, 131b, and so on. For example, a configuration may be taken in which the positioning pin 130 is biased towards the interior of the U-shape by a coil spring not illustrated to allow the tip to advance into the positioning holes 131a, 131b, and so on, while the user is able to extract the tip from the positioning holes 131a, 131b, and so on by pulling on the positioning pin 130. In addition, the user may also push the tip of the fixing screw 140 into an indentation by tightening the fixing screw 140, and thereby lock the two links 422c and 422d.

FIG. 10 illustrates a state of the passive slide mechanism 100 in which the slide amount of the other link 422d is changed with respect to the one link 422c. In FIG. 10, the positioning pin 130 is being inserted into the positioning hole 131b next to the positioning hole 131a in which the positioning pin 130 has been inserted in FIG. 6. In other words, the total length of the two links 422c and 422d in the state illustrated in FIG. 10 has become shorter than the total length of the two links 422c and 422d in the state illustrated in FIG. 6. By doing so, the user is able to lengthen and shorten the total length of the two links 422c and 422d, and alter the form of the arm unit 420 in accordance with the content or purpose of the surgical technique. Additionally, in the passive slide mechanism 100, since the two links 422c and 422d are locked, unexpected movement of the arm unit 420 during driving control of the support arm apparatus 400 may be prevented.

The numbers of the positioning holes 131a, 131b, and so on as well as the indentations are not particularly limited. However, in the support arm apparatus 400 according to the present embodiment, a control value used for driving control of the actuator 430 provided in the active joint units 421a to 421f by the control unit is selected from among control values preset in accordance with the form of the arm unit 420 selected by the passive slide mechanism 100. Consequently, if there is a large number of total lengths of the links 422c and 422d which can be set, the number of preset control values also increases. Thus, an appropriate number of the positioning holes 131a, 131b, and so on as well as the indentations may be formed in consideration of this point. For example, three each of positioning holes 131a, 131b, and 131c as well as indentations may be set at 10 cm intervals (see FIG. 10).

The configuration of the positioning pin 130 and the fixing screw 140 is not limited to the above example. Also, the configuration by which the two links 422c and 422d are positioned and the configuration by which the two links 422c and 422d are locked in the passive slide mechanism 100 are not limited to the examples described above.

In addition, the passive slide mechanism 100 may also be provided with a sensor 150 that detects the relative slide amount (displacement amount) of the two links 422c and 422d. By providing such a sensor 150, the slide amount of the passive slide mechanism 100 selected by the user is detected automatically by the control unit. With this arrangement, for example, the control unit is able to change the control values of the active joint units 421a to 421f in accordance with the displacement amount of the passive slide mechanism 100 detected by the sensor 150. Such a sensor 150 may by a non-contact optical sensor, for example.

Referring to FIG. 9, if describing a case in which using a transmissive photo interrupter is used as the sensor 150, for example, a transmissive photo interrupter is provided as the sensor 150 on the inner side of the bottom part of the one link 422c having a cross-sectional U-shape. Also, projecting parts 155 for position detection are formed on the outer side face of the bottom part of the other link 422d having a cross-sectional U-shape. Such projecting parts 155 are formed in equal number to the number of the positioning holes 131a, 131b, and so on, for example, and in a state in which one of the positioning holes 131a, 131b, and so on is inserted into the positioning pin 130, the corresponding projecting part may be positioned inside the transmissive photo interrupter.

In a state in which the positioning pin 130 is not inserted into any of the positioning holes 131a, 131b, and so on, a light-sensing part of the transmissive photo interrupter senses light emitted from a light-emitting part. On the other hand, in a state in which the positioning pin 130 is inserted into one of the positioning holes 131a, 131b, and so on, light from emitted from the light-emitting part is blocked by the projecting part 155, and is not sensed by the light-sensing part. At this point, the control unit may be configured to be able to detect the slide amount of the passive slide mechanism 100 by differentiating the arrangement state (such as the surface area or the position) of each projecting part 155 that is positioned inside the transmissive photo interrupter in the state in which the positioning pin 130 is inserted into each of the positioning holes 131a, 131b, and so on, for example.

The sensor 150 is not limited to a transmissive photo interrupter, and may also be a reflective photo interrupter, or any of various other types of sensors 150. Furthermore, in the technology of the present disclosure, the sensor 150 is not a required structural element, and the control unit may also be configured to acquire information about the slide amount of the passive slide mechanism 100 by having the user perform an input operation manually with respect to an input unit in accordance with the slide amount of the passive slide mechanism 100, for example.

Note that the passive slide mechanism 100 may also be configured by exchanging the two links 422c and 422d. In other words, in the passive slide mechanism 100 illustrated in FIG. 6, the link provided with the positioning pin 130 may be the link 422d on the front end side, while the link provided with the positioning holes 131a, 131b, and so on may be the link 422c on the root side.

(2-3-2. Passive Joint Unit)

FIGS. 11 to 13 are explanatory diagrams illustrating an exemplary configuration of the passive joint unit 200. FIG. 11 is a side view of the passive joint unit 200 as viewed from a direction orthogonal to a rotation axis Ax of the passive joint unit 200 and the longitudinal direction of the link 422d. FIG. 12 is a diagram of the passive joint unit 200 illustrated in FIG. 11 viewed from below, while FIG. 13 is a diagram of the III-III cross-section of the passive joint unit 200 illustrated in FIG. 11 viewed in the direction of the arrows.

The passive joint unit 200 of the support arm apparatus 400 according to the present embodiment joins the two links 422*d* and 422*e* disposed between the two active joint units 421*c* and 421*d* so as to allow the links to rotate with respect to each other. While the link 422*d* have a cross-sectional U-shape as described above, the link 422*e* has an approximately cylindrical shape. The passive joint unit 200 includes a base plate 220 attached to the one link 422*d*, and a movable part 210 that is supported via a bearing 225 so as to be able to rotate with respect to the base plate 220. The movable part 210 is configured as one end of the other link 422*e*. The rotation axis Ax is orthogonal to both the longitudinal direction of the link 422*d* and the longitudinal direction of the link 422*e*. For this reason, the movable part 210 configured on one end of the link 422*e* is supported by the base plate 220 in a direction orthogonal to the longitudinal direction of the link 422*e*. With this arrangement, relative rotation of the two links 422*d* and 422*e* becomes possible.

The base plate 220 is attached to the one link 422*d* by using fixing bolts 211, for example. In other words, as illustrated in FIG. 14, in the present embodiment, the passive joint unit 200 includes a mechanism in which the movable part 210 configured on one end of the other link 422*e* is rotatably supported with respect to the base plate 220, with such a base plate 220 and movable part 210 forming a unified body that is detachable from the one link 422*d*. The one link 422*d* includes an opening part 209 at a position opposing the base plate 220.

The base plate 220 is provided with an encoder 250. The encoder 250 is positioned inside the opening part 209 provided in the link 422*d*. The base plate 220 has a function of acting as an encoder case, and a support substrate 215 that supports a magnetic disc (permanent magnet) for the encoder 250 is disposed inside the base plate 220. The support substrate 215 is configured to be integrally rotatable with the movable part 210. Also, at the position opposing the magnetic disc on the support substrate 215 in the base plate 220, a magnetic field detecting element 255 that detects changes in the magnetic field due to the relative rotation of the magnetic disc is provided. With such an encoder 250, the relative rotational angle (displacement amount) of the two links 422*d* and 422*e* may be detected.

In the present embodiment, the passive joint unit 200 is able to set the rotational angle between the one link 422*d* and the other link 422*e* in multiple stages. In other words, the passive joint unit 200 is able to rotate the two links 422*d* and 422*e* by a rotational angle (displacement amount) preset in multiple stages. For example, a positioning pin 230 and a fixing screw 240 are provided on the base plate 220 secured to the one link 422*d*. The positioning pin 230 is able to advance towards the support substrate 215 in the extension direction of the rotation axis Ax, for example. The positioning pin 230 is disposed inside the opening part 209 provided in the link 422*d*. The fixing screw 240 is able to advance towards the support substrate 215 in the radial direction orthogonal to the rotation axis Ax, for example.

In addition, the support substrate 215 which is able to rotate integrally with the movable part 210 configured as one end of the other link 422*e* is provided with multiple positioning holes 231 that accept the tip of the positioning pin 230, and multiple cutouts 241 that accept the tip of the fixing screw 240. However, in FIG. 13, only one each of the positioning holes 231 and the cutouts 241 is illustrated. The positioning holes 231 are provided penetrating the support substrate 215 in the extension direction of the rotation axis Ax. The cutouts 241 are formed by cutting out depressions in part of the outer circumferential surface of the support substrate 215. The cutouts 241 are provided at positions allowing the tip of the fixing screw 240 to advance in a state in which the positioning pin 230 is able to advance with respect to each of the positioning holes 231. In other words, in the example of the passive joint unit 200 illustrated, the disposed positions of the multiple positioning holes 231 and the disposed positions of the multiple cutouts 241 have a 180 degree phase offset about the rotation axis Ax as the center.

The user sets the angle obtained between the two links 422*d* and 422*e* by inserting the tip of the positioning pin 230 into a selected one of the positioning holes 231. For example, a configuration may be taken in which the positioning pin 230 is biased towards the positioning holes 231 by a coil spring not illustrated to allow the tip to advance into the positioning holes 231, while the user is able to extract the tip from the positioning holes 231 by pulling on the positioning pin 230. In addition, the user pushes the tip of the fixing screw 240 into a cutout 241 by tightening the fixing screw 240, thereby locking the two links 422*d* and 422*e*. By doing so, the user is able to change the angle obtained between the two links 422*d* and 422*e*, and alter the form of the arm unit 420 in accordance with the content or purpose of the surgical technique. Additionally, in the passive joint unit 200, since the two links 422*d* and 422*e* are locked, unexpected movement of the arm unit 420 during driving control of the support arm apparatus 400 may be prevented.

The numbers of the positioning holes 231 and the cutouts 241 are not particularly limited. However, in the support arm apparatus 400 according to the present embodiment, a control value used for driving control of the actuator 430 provided in the active joint units 421*a* to 421*f* by the control unit is selected from among control values preset in accordance with the form of the arm unit 420 selected by the passive joint unit 200. Consequently, if there is a large number of rotational angles of the links 422*d* and 422*e* which can be set, the number of preset control values also increases. Thus, an appropriate number of the positioning holes 231 and the cutouts 241 may be formed in consideration of this point. For example, six each of the positioning holes 231 and the cutouts 241 may be set at 22.5 degree intervals.

The configuration of the positioning pin 230 and the fixing screw 240 is not limited to the above example. Also, the configuration by which the base plate 220 and the support substrate 215 are positioned and the configuration by which the base plate 220 and the support substrate 215 are locked are not limited to the examples described above.

In addition, the passive joint unit 200 is provided with an encoder 250 that acts as a sensor to detect the relative rotational angle (displacement amount) of the two links 422*d* and 422*e*. By providing such an encoder 250, the rotational angle of the passive joint unit 200 selected by the user is detected automatically by the control unit. With this arrangement, for example, the control unit is able to change the control values of the active joint units 421*a* to 421*f* in accordance with the displacement amount of the passive joint unit 200 detected by the encoder 250. Note that the sensor that detects the rotational angle of the passive joint unit 200 is not limited to the encoder 250. Furthermore, in the technology of the present disclosure, the encoder 250 is not a required structural element, and the control unit may also be configured to acquire information about the rotational angle of the passive joint unit 200 by having the user perform an input operation manually with respect to an input unit in accordance with the rotational angle of the passive joint unit 200, for example.

Note that the passive joint unit 200 may also be configured by exchanging the two links 422*d* and 422*e*. In other words, in the passive joint unit 200 illustrated in FIG. 11, the link provided with the base plate 220 and the movable part 210 may be the link 422d on the root side, while the link to which the base plate 220 is secured may be the link 422e on the front end side.

In this way, the support arm apparatus 400 according to the present embodiment is provided with the passive slide mechanism 100 and the passive joint unit 200 as a passive form modification mechanism by which the form of the arm unit 420 may be changed. Consequently, when disposing the support arm apparatus 400 before the beginning of surgery, or when a large expansion of the field of view becomes necessary during surgery, for example, the movable range of the arm unit 420 can be set appropriately in accordance with the content or purpose of the surgical technique.

Also, in the passive slide mechanism 100, the one link 422c and the other link 422d can be decoupled by detaching the slider 120 provided on the other link 422d from the rail part 110 provided on the one link 422c. Furthermore, in the passive joint unit 200, the one link 422d and the other link 422e can be decoupled by removing the base plate 220 from the one link 422d. Consequently, for example, the form of the arm unit 420 can also be altered by replacing the configuration portion of the arm unit 420 that is on the front end side past the passive slide mechanism 100 or the passive joint unit 200 with another configuration portion having different link lengths or the like, while also securing an electrical connection by using connectors or the like. With this arrangement, a more general-purpose support arm apparatus 400 which may be adapted to suit the content or purpose of a variety of surgical techniques can be obtained.

3. EXEMPLARY CONFIGURATION OF CONTROL APPARATUS

The above thus describes a configuration of the support arm apparatus 400 according to the present embodiment. Hereinafter, an exemplary configuration of a control apparatus 350 for conducting driving control of the arm unit 420 in the support arm apparatus 400 according to the present embodiment, or in other words, for controlling the rotational driving of the actuator 430 provided in the active joint units 421a to 421f, will be described.

FIG. 15 is a block diagram illustrating an overall configuration example of the support arm apparatus 400 including a control apparatus 350. The control apparatus 350 is provided with a control unit 351, a storage unit 357, and an input unit 359.

The control unit 351 is made up of any of various types of signal processing circuits, such as a CPU or a DSP, for example. The control unit 351 centrally controls the control device 350, while also performing various computations for controlling the driving of the arm unit 420 in the support arm apparatus 400. Specifically, the control unit 351 includes a whole body cooperative control unit 353 and an ideal joint control unit 355. The whole body cooperative control unit 353 performs various computations for whole body cooperative control in order to control the driving of the actuator 430 provided in the active joint units 421a to 421f of the arm unit 420 of the support arm apparatus 400. The ideal joint control unit 355 performs various computations for ideal joint control that realize an ideal response with respect to whole body cooperative control by correcting the influence of disturbances. The storage unit 357 may be a storage element such as random access memory (RAM) or read-only memory (ROM), for example, or alternatively, may be semiconductor memory, a hard disk, or an external storage device.

The input unit 359 is an input interface by which the user inputs information, commands, and the like related to the driving control of the support arm apparatus 400 into the control unit 351. The input unit 359 includes an operating mechanism operated by the user, such as a lever or a pedal, for example, and in response to the operation such a level, pedal, or the like, information such as the position and velocity of each component member of the arm unit 420 may be set as an instantaneous purpose of motion. Such an input unit 359 may also include another operating mechanism operated by the user besides a level or pedal, for example, such as a mouse, a keyboard, a touch panel, buttons, and switches.

<3-1. Whole Body Cooperative Control>

The whole body cooperative control unit 353 performs various computations related to whole body cooperative control using generalized inverse dynamics. For example, the whole body cooperative control unit 353 acquires information about the state of the arm unit 420 on the basis of the rotational angle and the loaded torque of each of the active joint units 421a to 421f detected by components such as torque sensors and encoders provided in the active joint units 421a to 421f. Additionally, the whole body cooperative control unit 353 uses generalized inverse dynamics to compute control values for whole body cooperative control of the arm unit 420 in an operation space, on the basis of factors such as the state of the arm unit 420, the purpose of motion for the arm unit 420, and constraint conditions. Note that the operation space is a space for describing the relationship between the force acting on the arm unit 420 and the acceleration produced in the arm unit 420, for example.

Generalized inverse dynamics is a basic computation for whole body cooperative control of a multi-link structure made up of multiple links joined together by multiple active joint units (in the present embodiment, this corresponds to the arm unit 420 illustrated in FIG. 3, for example), in which a purpose of motion related to various dimensions in various types of operation spaces is converted into torques to be generated in multiple active joint units, while also accounting for various constraint conditions.

An operation space is an important concept for force control of a robot apparatus such as a support arm apparatus. An operation space is a space for describing the relationship between the force acting on a multi-link structure and the acceleration of the multi-link structure. When controlling the driving of a multi-link structure by force control rather than position control, the concept of an operation space becomes necessary in the case of using the way in which the multi-link structure and the environment interact as a constraint condition. An operation space is a space to which the multi-link structure belongs, such as a joint space, a Cartesian space, or a momentum space, for example.

The purpose of motion expresses a target value for driving control of the multi-link structure. For the purpose of motion, tasks such as "maintain viewpoint of imaging unit" (in other words, keep the position and the attitude of the endoscopic device 423 constant) and "secure field of view for surgeon" (in other words, do not allow the arm unit 420 and the endoscopic device 423 to intrude into the surgeon's field of view) may be set. In actual control, more specifically, target values for factors such as the position, velocity, acceleration, force, and impedance of the multi-link structure for achieving these tasks may be set.

In addition, the purpose of motion may also be a power assist operation that controls the generated torque in each of the active joint units 421a to 421f so as to cancel out gravity acting on the arm unit 420 (gravity compensation control), and also controls the generated torque in the active joint units 421*a* to 421*f* to assist the movement of the arm unit 420 in the direction of a force applied additionally from outside. Specifically, in a power assist operation, by controlling the driving of the actuator 430 provided in each of the active joint units 421*a* to 421*f* so as to generate in each of the active joint units 421*a* to 421*f* a generated torque that cancels out the external torque due to gravity in each of the active joint units 421*a* to 421*f* of the arm unit 420, the position and the attitude of the arm unit 420 are maintained in a certain state.

In this state, in a case in which external torque is applied additionally from outside (for example, from the user), the driving of the actuator 430 provided in each of the active joint units 421*a* to 421*f* is controlled so that a generated torque in the same direction as the applied external torque is generated in each of the active joint units 421*a* to 421*f*. By conducting such a power assist operation, in a case in which the user moves the arm unit 420 manually, the user is able to move the arm unit 420 with less force. For this reason, it is possible to impart to the user a feeling of moving the arm unit 420 as if in a weightless environment, thereby improving the operability of the arm unit 420 for the user.

Constraint conditions are constraint conditions related to factors such as the position, velocity, acceleration, and force of the multi-link structure, which are determined by shape and structure of the multi-link structure, the environment surrounding the multi-link structure, settings set by the user, and the like. For example, the constraint conditions include information about factors such as generated force, priority, the presence or absence of non-driven joints, vertical reaction force, friction weighting, and a support polygon. Constraint conditions may be set in accordance with the purpose of motion. For example, if the purpose of motion is to "maintain viewpoint of imaging unit", geometric restrictions are imposed as constraint conditions on the front end position (fingertip position) and front end attitude (fingertip attitude) of the arm unit 420, so as to keep the fingertip position and the fingertip attitude in a certain state. As another example, if the purpose of motion is to "secure field of view for surgeon", restrictions are imposed as constraint conditions on the movement range, so that the arm unit 420 and the endoscopic device 423 do not intrude into a certain invasion prohibition region set in space. For the invasion prohibition region, a region anticipated to be the region of the surgeon's field of view is set appropriately.

At this point, in generalized inverse dynamics used when executing whole body cooperative control, to achieve both stability in numerical calculations and computational efficiency enabling real-time processing, the computational algorithm is made up of a first stage of a virtual force decision process (virtual force computation process), and a second stage of an actual force conversion process (actual force computation process). In the first stage of the virtual force computation process, the virtual force, which is a virtual force acting on the operation space necessary for achieving each purpose of motion, is decided while also accounting for the priority of the purpose of motion and a maximum value of the virtual force. In the second stage of the actual force computation process, the virtual force obtained above is converted into actual force realizable with the configuration of the actual multi-link structure, such as joint force and external force, while also accounting for constraints related to non-driven joints, vertical reaction force, friction weighting, a support polygon, and the like. Hereinafter, the virtual force computation process and the actual force computation process will be described in detail.

(3-1-1. Virtual Force Computation Process)

Let a generalized variable q be a vector made up of a certain physical quantity in each joint unit of a multi-link structure (also called the joint value q or the joint space q). An operation space x is defined by Formula (1) below, using the generalized variable q and the Jacobian J.

[Math.1]

$$\dot{x} = J\dot{q} \tag{1}$$

Given the configuration of the support arm apparatus 400 according to the present embodiment, for example, x in the above Formula (1) is the front end position of the active joint units 421*a* to 421*f* of the arm unit 420, while q is the rotational angle in the active joint units 421*a* to 421*f* of the arm unit 420. An equation of motion related to the operation space x is stated by Formula (2) below.

[Math.2]

$$\ddot{x} = \Lambda^{-1} f + c \tag{2}$$

Herein, f represents the force acting on the operation space x. Also, $\Lambda^{-1}$ is the inverse inertia matrix of the operation space, while c is called the bias acceleration of the operation space. These quantities are expressed in Formulas (3) and (4) below, respectively.

[Math.3]

$$\Lambda^{-1} = J H^{-1} J^T \tag{3}$$

$$c = J H^{-1} (\tau - b) + \dot{J}\dot{q} \tag{4}$$

Note that H is the inertia matrix of the joint space, τ is the joint force corresponding to the joint value q (for example, the generated torque in the joint units 511*a* to 511*f*), and b is a term representing the gravitational force, the Coriolis force, and the centrifugal force.

In generalized inverse dynamics, it is known that target values of the position and velocity related to the operation space x corresponding to a purpose of motion can be expressed as the acceleration of the operation space x. At this point, from Formula (1) above, to realize an operation space acceleration which is a target value given in accordance with a purpose of motion, the virtual force $f_v$ to act on the operation space x is obtained by solving a type of linear complementary problem (LCP) like Formula (5) below.

[Math. 4]

$$w + \ddot{x} = \Lambda^{-1} f_v + c \tag{5}$$

$$\text{s.t.} \begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Herein, $L_i$ and $U_i$ are taken to be the negative lower-bound value (including $-\infty$) of the ith component of and the positive upper-bound value (including $+\infty$) of the ith component of $f_v$, respectively. The above LCP can be solved using a method of applying the iterative method, the pivot method, robust acceleration control, or the like, for example.

Note that the inverse inertia matrix $\Lambda^{-1}$ of the operation space and the bias acceleration c have a large calculation cost if computed according to the definitions of these terms in Formulas (3) and (4) above. Consequently, there is proposed a method of carrying out the process of computing the inverse inertia matrix $\Lambda^{-1}$ of the operation space more quickly by applying forward dynamics (FWD) computations, which obtain a generalized acceleration (joint acceleration) from the generalized force (joint force T) of the multi-link structure. Specifically, by using forward dynamics (FWD) computations, the inverse inertia matrix $\Lambda^{-1}$ of the operation space and the bias acceleration c can be obtained from information related to forces acting on the multi-link structure, such as the joint space q, the joint force T, and gravity g. In this way, by applying forward dynamics (FWD) computations related to the operation space, the inverse inertia matrix $\Lambda^{-1}$ of the operation space can be calculated with a computational complexity O(N) with respect to the number N of joint units.

At this point, as an example setting of a target value corresponding to a purpose of motion, a condition for achieving a target value of the operation space acceleration (indicated by the superscript bar over the second derivative of x) with a virtual force $f_{vi}$ that is less than or equal to the absolute value of $F_i$ can be expressed by Formula (6) below.

[Math.5]

$$L_i = -F_i,$$

$$U_i = F_i,$$

$$\ddot{x}_i = \ddot{\bar{x}}_i \tag{6}$$

Also, as described above, the target value related to the position and velocity of the operation space x can be expressed as a target value of the operation space acceleration, specifically by Formula (7) below (the position and velocity of the operation space x are indicated by a superscript bar over x and the first derivative of x).

[Math.6]

$$\ddot{\bar{x}}_i = K_P(\bar{x}_i - x_i) + K_v(\dot{\bar{x}}_i - \dot{x}_i) \tag{7}$$

Otherwise, by using the concept of a decomposed operation space, a target value related to an operation space expressed as a linear sum of other operation spaces (such as momentum, Cartesian relative coordinates, or linked joints) can also be set.

(3-1-2. Actual Force Computation Process)

In the second stage of the actual force computation process in generalized inverse dynamics, a process if conducted to replace the virtual force obtained by (3-1-1. Virtual force computation process) above with actual joint force and external force. A condition for realizing the generalized force $\tau_v = J_v^T f_v$ according to the virtual force with the generated torque $\tau_a$ generated in the joint units and the external force $f_e$ is expressed by Formula (8) below.

[Math. 7]

$$\begin{bmatrix} J_{vu}^T \\ J_{va}^T \end{bmatrix}(f_v - \Delta f_v) = \begin{bmatrix} J_{eu}^T \\ J_{ea}^T \end{bmatrix} f_e + \begin{bmatrix} 0 \\ \tau_a \end{bmatrix} \tag{8}$$

Herein, the subscript a denotes the set of driven joint units (driven joint set), while the subscript u denotes the set of non-driven joint units (non-driven joint set). In other words, the upper part of Formula (8) above expresses the equilibrium of forces in the space according to the non-driven joint units (non-driven joint space), while the lower part expresses the equilibrium of forces in the space according to the driven joint units (driven joint space). $J_{vu}$ and $J_{va}$ are, respectively, the non-driven joint component and the driven joint component of the Jacobian related to the operation space in which the virtual force acts. $J_{eu}$ and $J_{ea}$ are, respectively, the non-driven joint component and the driven joint component of the Jacobian related to the operation space in which the external force $f_e$ acts. $\Delta f_v$ expresses the component of the virtual force which is not realizable by actual force.

The upper part of Formula (8) above is uncertain, and by solving a quadratic programming (QP) problem as indicated in Formula (9) below, for example, $f_e$ and $\Delta f_v$ can be obtained.

[Math.8]

$$\min \tfrac{1}{2}\varepsilon^T Q_1 \varepsilon + \tfrac{1}{2}\xi^T Q_2 \xi$$

$$s.t. U\xi \geq v \tag{9}$$

Herein, $\varepsilon$ is the difference between both sides of the upper part of Formula (8) above, and expresses the equality error of Formula (8). Meanwhile, $\xi$ is the concatenated vector of $f_e$ and $\Delta f_v$, and expresses a variable vector. $Q_1$ and $Q_2$ are positive definite symmetric matrices expressing weights for the case of minimization. Also, the inequality constraint in Formula (9) above is used to express a constraint condition related to the external force, corresponding to the set purpose of motion, such as vertical reaction force, friction weighting, maximum value of the external force, and a support polygon.

For example, an equality constraint related to a rectangular support polygon is expressed in Formula (10) below.

[Math.9]

$$|F_x| \leq \mu_t F_z,$$

$$|F_y| \leq \mu_t F_z,$$

$$F_z \geq 0,$$

$$|M_x| \leq d_y F_z,$$

$$|M_y| \leq d_x F_z,$$

$$|M_z| \leq \mu_r F_z \tag{10}$$

Herein, z represents the normal direction of the contact plane, while x and y represent the two orthogonal tangent directions perpendicular to z. $(F_x, F_y, F_z)$ and $(M_x, M_y, M_z)$ are the external force and the external moment acting on the contact point. $\mu_t$ and $\mu_r$ are coefficients of friction related to translation and rotation, respectively. $(d_x, d_y)$ expresses the size of the support polygon.

For example, from Formulas (9) and (10) above, the minimum norm or the solution $f_e$, $\Delta f_v$ of the minimum error is computed. By substituting $f_e$ and $\Delta f_v$ obtained from Formula (9) above into Formula (8) above, the joint force $\tau_a$ necessary for realizing the purpose of motion, or in other words, the generated torque $\tau_a$ in each of the active joint units 421a to 421f can be obtained.

In actual practice, a constraint condition corresponding to the set purpose of motion is set by appropriately formulation, like in Formula (10) above.

In the case of a system in which the bases are fixed, and there are no non-driven joints, all virtual forces are replaceable with joint forces only, and in Formula (8) above, $f_e = 0$ and $\Delta f_v = 0$ can be set. In this case, from the bottom part of Formula (8) above, the following Formula (11) can be obtained for the joint force $\tau_a$.

[Math.10]

$$\tau_a = J_{va}^T f_v \quad (11)$$

The above thus describes an example of whole body cooperative control using generalized inverse dynamics. As described above, by successively conducting a virtual force computation process and an actual force computation process, the joint force $\tau_a$ for achieving a desired purpose of motion can be obtained. In other words, in the opposite sense, by treating a computed joint force $\tau_a$ as a control value for the driving control of the active joint units 421a to 421f, the active joint units 421a to 421f may be driven to achieve a desired purpose of motion.

Note that regarding the whole body cooperative control using generalized inverse dynamics described so far, particularly details such as the process of deriving the virtual force $f_v$, the method of solving the above LCP to find the virtual force $f_v$, and the solution of the QP problem, literature such as JP 2009-95959A and JP 2010-188471A submitted previously by the applicant can be referenced, for example.

<3-2. Ideal Joint Control Unit>

The ideal joint control unit 355 performs various computations for ideal joint control that realize an ideal response with respect to whole body cooperative control by correcting the influence of disturbances. Hereinafter, an example of ideal joint control will be described. The motion of the actuator 430 provided in each of the active joint units 421a to 421f of the support arm apparatus 400 is modeled by the equation of second-order lag motion expressed in Formula (12) below.

[Math.11]

$$I_a \ddot{q}^{ref} = \tau_a + \tau_e - v_a \dot{q} \quad (12)$$

Herein, q is the rotational angle of the actuator 430, $q^{ref}$ is a rotational angle target value of the actuator 430, $I_a$ is the inertial moment of the actuator 430, $\tau_a$ is the generated torque of the actuator 430, $\tau_e$ is the external torque acting on the actuator 430 from the outside, and $v_a$ is a viscous drag coefficient for the actuator 430. The above Formula (12) is a theoretical model expressing the motion of the actuator 430 in each of the active joint units 421a to 421f.

As described in (3-1. Whole body cooperative control) above, the torque $\tau_a$ that the actuator 430 in each of the active joint units 421a to 421f should generate (generated torque $\tau_a$) to realize a task can be computed with computation using generalized inverse dynamics. Ideally, by applying the generated torque $\tau_a$ computed for each actuator 430 to Formula (12) above, a response obeying the theoretical model expressed in Formula (12) above should be realized in each actuator 430, or in other words, the desired operation should be realized in the arm unit 420.

However, in actuality, the influence of various disturbances causes error (modeling error) to occur between the actual motion in the actuator 430 and the theoretical model expressed in Formula (12) above in some cases. Modeling error may be divided roughly into error arising from mass properties, such as the mass, center of gravity, and inertia tensor of a multi-link structure (in other words, the arm unit 420 to be controlled), and error arising from factors such as friction and inertia internal to the actuator 430. Of these, the former modeling error arising from mass properties may be reduced comparatively easily during construction of the theoretical model by increasing the precision of computer-aided design (CAD) data and applying identification techniques.

On the other hand, the latter modeling error arising from factors such as friction and inertia internal to the actuator 430 is caused by phenomena which are difficult to model, such as friction in the reduction gear, for example. Consequently, modeling error non-negligible modeling error may still remain during construction of the theoretical model which indicates the motion of the actuator 430. Additionally, there is also a possibility of error occurring between the values of the inertia $I_a$ and the viscous drag coefficient $v_a$ in Formula (1) above, and these values in the actual actuator 430. These difficult-to-model errors arising from factors such as friction and inertia internal to the actuator 430 may become disturbances in the driving control of the actuator 430. Thus, because of the influence of such disturbances, in actuality, cases occur in which the motion of the actuator 430 does not respond exactly like the theoretical model expressed in Formula (12) above, or in other words, the desired operation is not realized.

Accordingly, in the present embodiment, an active control system is added to the actuator 430 to thereby correct the response of the actuator 430 so as to perform ideal response obeying the theoretical model expressed in Formula (12) above. Note that controlling the driving of the actuator 430 so that the actuators 430 of the support arm apparatus 400 (that is, the active joint units 421a to 421O perform ideal response as expressed in Formula (12) above in this way is designated ideal joint control in the present embodiment.

Note that for details about ideal joint control, literature such as JP 2009-269102 submitted previously by the applicant can be referenced, for example.

<3-3. Application of Mass Property Information of Arm Unit>

Herein, between the whole body cooperative control and the ideal joint control described above, geometric information about the arm unit 420 is aggregated in the Jacobian J included in the computational formulas for whole body cooperative control (for example, Formulas (1), (3), (4), (8), and (11)). For this reason, in a case in which mass properties such as the weight, center of gravity, and inertial tensor of the arm unit 420 as a whole are changed, the information in the Jacobian J which is used also has to be changed. In the support arm apparatus 400 according to the present embodiment, the form of the arm unit 420 may be changed by passive form modification mechanisms, and thus the information in the Jacobian J (control values) used during whole body cooperative control by the whole body cooperative control unit 353 also has to be changed in accordance with the form of the arm unit 420. As an example, a shifting of the center of gravity of the arm unit 420 in accordance with the displacement amount of a passive form modification mechanism will be described.

FIG. 16 is an explanatory diagram illustrating how the center of gravity of the arm unit 420 shifts because of a difference in the total length of the link 422c and the link 422d due to a difference in the slide amount of the passive slide mechanism 100. It is demonstrated that as the total length of the two links 422c and 422d becomes longer because of the passive slide mechanism 100, the center of gravity changes position from C1 to C2. Also, FIG. 17 is an explanatory diagram illustrating how the center of gravity of the arm unit 420 shifts because of a difference in the angle obtained between the link 422d and the link 422e due to a difference in the rotational angle of the passive joint unit 200. It is demonstrated that as the angle obtained between the two links 422d and 422e changes because the passive joint unit 200, the center of gravity changes position from C3 to C4.

Accordingly, the whole body cooperative control unit 353 is configured to be able to execute whole body cooperative control appropriately on the basis of the displacement amounts of the passive form modification mechanisms. Specifically, the storage unit 357 of the control apparatus 350 stores mass property information corresponding to the displacement amount of the passive form modification mechanisms, and the whole body cooperative control unit 353 executes whole body cooperative control using the information in a Jacobian J (control values) generated on the basis of the mass property information corresponding to the displacement amounts detected by sensors provided in the passive form modification mechanisms. In the support arm apparatus 400 according to the present embodiment, the total length of the two links 422c and 422d which may be set by the passive slide mechanism 100 may be set in three patterns, for example. Also, the angle obtained between the two links 422d and 422e which may be set by the passive joint unit 200 may be set in six patterns, for example. Consequently, the storage unit 357 may store 18 patterns (3 patterns×6 patterns) of mass property information, for example.

For example, when installing the arm unit 420 on an operating table or the like that acts as the base unit 410 before surgery is begun, or when a large expansion of the field of view becomes necessary during surgery, the user changes the displacement amounts of the passive form modification mechanisms. When the user operates the passive form modification mechanisms, an input operation may be performed on the input unit 359 to apply a brake to the actuator 430 provided in the active joint units 421a to 421f, and attitude changes of the arm unit 420 may be prohibited temporarily. Other than the point about the information in the Jacobian J to be used being changed in accordance with the displacement amounts of the passive form modification mechanisms, whole body cooperative control of the arm unit 420 may be conducted in accordance with the computational processes described earlier. Also, ideal joint control likewise may be conducted in accordance with the computational processes described earlier, in accordance with the computational results obtained by the whole body cooperative control unit 353.

In this way, by having the whole body cooperative control unit 353 conduct whole body cooperative control using control values generated on the basis of mass property information selected in accordance with the displacement amounts of the passive form modification mechanisms, the accuracy of gravity compensation control can be raised in accordance with shifts in factors such as the center of gravity due to changes in the form of the arm unit 420. As a result, the load acting on the active joint units 421a to 421c disposed on the root side of the arm unit 420 can be reduced, and the actuator 430 provided in components such as these active joint units 421a to 421c can be miniaturized.

In addition, in the case in which the support arm apparatus 400 is provided with, at the root portion of the arm unit 420, an attitude sensor 450 for detecting the inclination of the arm unit 420 overall with respect to the horizontal direction, the whole body cooperative control unit 353 may also execute whole body cooperative control by additionally using the inclination of the arm unit 420 detected by such an attitude sensor 450. By using information about the inclination of the arm unit 420 overall, the gravity acting on the arm unit 420 can be computed accuracy, and the accuracy of gravity compensation control can be raised further. For example, it is possible to moderate decreases in the accuracy of gravity compensation control in correspondence with the inclination of an operating table in the case in which the arm unit 420 is mounted onto the operating table as the base unit 410.

4. EXAMPLE OF CONTROL METHOD OF SUPPORT ARM APPARATUS

Referring to FIG. 18, the processing sequence of a control method of the arm unit 420 of the support arm apparatus 400 according to the present embodiment will be described briefly. FIG. 18 is a flowchart illustrating an example of a processing sequence of a control method of the arm unit 420 of the support arm apparatus 400 according to the present embodiment.

In the control method of the arm unit 420 of the support arm apparatus 400 according to the present embodiment, first, the whole body cooperative control unit 353 acquires the displacement amount of a passive form modification mechanism (step S101). For example, the slide amount of the passive slide mechanism 100 and the rotational angle of the passive joint unit 200 are detected, on the basis of information detected by the sensor 150 and the encoder 250 provided in the passive slide mechanism 100 and the passive joint unit 200 which act as passive form modification mechanisms. Instead of using detection information from the sensor 150 and the encoder 250, information about the slide amount of the passive slide mechanism 100 and the rotational angle of the passive joint unit 200 may also be input via the input unit 359.

Subsequently, the whole body cooperative control unit 353 sets mass property information of the arm unit 420 on the basis of the acquired displacement amount of the passive form modification mechanism (step S103). In the support arm apparatus 400 according to the present embodiment, the slide amount of the passive slide mechanism 100 and the rotational angle of the passive joint unit 200 which can be set are respectively preset in multiple stages. For this reason, the whole body cooperative control unit 353 selects mass property information corresponding to the current combination of the slide amount of the passive slide mechanism 100 and the rotational angle of the passive joint unit 200 from among mass property information prestored in the storage unit 357 in correspondence with combinations of respective slide amounts of the passive slide mechanism 100 and respective rotational angles of the passive joint unit 200. With this arrangement, the Jacobian J to be used in Formula (1) above is set in accordance with the form of the arm unit 420.

Next, the whole body cooperative control unit 353 acquires the arm state, on the basis of the states of the active joint units 421a to 421f (step S105). The states of the active joint units 421a to 421f refers to factors such as the rotational angle or the generated torque of the active joint units 421a to 421f, for example. In addition, the arm state is the state of motion of the arm unit 420, and is the position, velocity, acceleration, force, and the like of the arm unit 420, for example. The whole body cooperative control unit 353 is able to detect the rotational angle or the generated torque of each of the active joint units 421a to 421f on the basis of detection signals from the encoder and torque sensor provided in each of the active joint units 421a to 421f.

Next, the whole body cooperative control unit 353 sets an operation condition (step S107). For example, the whole body cooperative control unit 353 sets a purpose of motion specified by the user and a constraint condition corresponding to the purpose of motion as an operation condition for calculating a control value (the generated torque $\tau_a$ described above) for driving the arm unit 420 to execute the purpose of motion. The operation condition set at this time reflects the current mass property information of the arm unit 420 set in step S103 above.

Next, the whole body cooperative control unit 353 performs operations for whole body cooperative control using generalized inverse dynamics on the basis of the arm state and the operation condition, and computes the generated torque $\tau_a$ for each of the active joint units 421a to 421f (step S109). In step S109, the whole body cooperative control unit 353 first computes the virtual force to act on each of the active joint units 421a to 421f of the arm unit 420 which is necessary for executing the purpose of motion set in step S107. Next, on the basis of the computed virtual force, the whole body cooperative control unit 353 computes the generated torque $\tau_a$ for each of the active joint units 421a to 421f by computing the actual force to actually act on each of the active joint units 421a to 421f of the arm unit 420 which is necessary for executing the purpose of motion set in step S107.

Next, the ideal joint control unit 355 performs operations for ideal joint control, and computes a torque command value T from the generated torque $\tau_a$ (step S111). Specifically, the ideal joint control unit 355 computes a disturbance estimate value $\tau_d$, which is a torque value due to a disturbance, and uses the disturbance estimate value $\tau_d$ to compute the torque command value $\tau$, which is a command value expressing the torque to be generated ultimately by the active joint units 421a to 421f of the arm unit 420.

Next, on the basis of the computed torque command value $\tau$, the ideal joint control unit 355 outputs drive command signals to driving circuits of the active joint units 421a to 421f of the arm unit 420 which are not illustrated (step S113). With this arrangement, the arm unit 420 becomes driven so that the purpose of motion set in step S107 may be executed in accordance with the current form (mass properties) of the arm unit 420.

5. MODIFICATIONS

The foregoing thus describes an exemplary configuration and an example of a processing sequence of a control method of the support arm apparatus 400 according to the present embodiment. Hereinafter, modifications of the support arm apparatus 400 according to the present embodiment will be described.

In the support arm apparatus 400 according to the present embodiment, the form of the arm unit 420 may change depending on the displacement amount of a passive form modification mechanism, and cases such as when the slide amount of the passive slide mechanism 100 is maximized, for example, the gravity acting on the active joint units disposed on the root side of the arm unit 420 increases in some cases. Also, the weight of the passive slide mechanism 100 or the passive joint unit 200 itself being added to the weight of the arm unit 420 causes the gravity acting on the active joint units disposed on the root side of the arm unit 420 to increase in some cases. Even in such cases, to prevent increased bulk of the actuator 430 provided in such active joint units in order to accommodate the increased load on the actuator 430, at least a subset of such active joint units may also be provided with a gravity compensation mechanism. A gravity compensation mechanism imparts to an active joint unit a torque (hereinafter also called a "compensating torque") in the direction of canceling out the load torque due to the weight of the arm unit 420 itself acting on that active joint unit. Such a gravity compensation mechanism may be a gravity compensation mechanism utilizing elastic force from a spring, for example.

FIG. 19 illustrates an exemplary configuration of a support arm apparatus 400 provided with gravity compensation mechanisms 460 and 470. In the support arm apparatus 400 illustrated in FIG. 19, gravity compensation mechanisms 460 and 470 are provided in the active joint units 421b and 421c which mainly conduct pitching from among the active joint units 421a to 421c disposed on the root side of the arm unit 420 for deciding the rough position of an endoscopic device or the like supported on the front end of the arm unit 420.

The gravity compensation mechanism 460 is made up of a hooking part 461 which is securely provided with respect to the link 422b connected to the front end side of the active joint unit 421b (in other words, the hooking part 461 rotates together with the link 422b about the active joint unit 421b), and a spring 463 stretched between the hooking part 461 and the link 422a connected to the root side of the active joint unit 421b. Similarly, the gravity compensation mechanism 470 is made up of a hooking part 471 which is securely provided with respect to the link 422c connected to the front end side of the active joint unit 421c, and a spring 473 stretched between the hooking part 471 and the link 422b connected to the root side of the active joint unit 421c.

By such gravity compensation mechanisms 460 and 470, in the case in which the configurations on the front end side from the links 422b and 422c rotate respectively about the active joint units 421b and 421c in the direction of gravity acting on the configurations on the front end side from the links 422b and 422c, the springs 463 and 473 extend in accordance with the rotation amount. At this time, the restoring force of the extended springs 463 and 473 acts on the configurations on the front end side from the links 422b and 422c to rotate the configurations on the front end side from the links 422b and 422c in the reverse direction of the rotation in the direction of gravity about the active joint units 421b and 421c. In other words, the restoring force of the springs 463 and 473 imparts to the active joint units 421b and 421c a compensating torque in a direction that cancels out the load torque due to the weights themselves of the configurations on the front end side from the links 422b and 422c acting on the active joint units 421b and 421c.

The springs 463 and 473 are tension springs, for example. Otherwise, any of various known types of springs, such as compression springs and torsion coil springs, for example, may be used as the springs 463 and 473. Alternatively, instead of the springs 463 and 473, other elastic bodies that produce a restoring force in response to expansion or contraction may be used.

The gravity compensation mechanisms 460 and 470 above have a simple configuration made up of the hooking parts 461 and 471, and the springs 463 and 473. By such a configuration, in the gravity compensation mechanisms 460 and 470, the restoring force of the springs 463 and 473 has a simple positive correlation of increasing as the rotational angle in the active joint units 421b and 421c increases, and decreasing as the rotational angle decreases. In other words, the restoring force of the springs 463 and 473 may vary monotonically with respect to the rotational angle in the active joint units 421b and 421c. The value of the compensating torque generated by the gravity compensation mechanisms 460 and 470 for the current attitude of the arm unit 420 may be computed on the basis of information about the rotational angle of the active joint units 421b and 421c.

Accordingly, the whole body cooperative control unit 353 may perform gravity compensation by additionally accounting for the compensating torque imparted to the active joint units 421b and 421c by the gravity compensation mechanisms 460 and 470, and driving the actuator 430 provided in the active joint units 421b and 421c so that the load torque due to the weight of the arm unit 420 itself may be canceled out. In other words, the whole body cooperative control unit 353 may impart a torque to each of the active joint units 421b and 421c with the actuator 430, so as to compensate for the insufficiency which cannot be fully compensated for by the gravity compensation mechanisms 460 and 470, namely the result obtained by subtracting the compensating torque imparted to the active joint units 421b and 421c by the gravity compensation mechanisms 460 and 470 from the load torque due to the weight of the arm unit 420 itself acting on the active joint units 421b and 421c.

Specifically, when computing the generated torque $\tau_a$ in step S109 in the flowchart described earlier (FIG. 18), the whole body cooperative control unit 353 computes the generated torque $\tau_a$ by treating the result of subtracting the compensating torque from the load torque due to the weight of the arm unit 420 itself as the gravitational component due to the weight of the arm unit 420 itself. With this arrangement, there is computed a generated torque $\tau_a$ that should be generated in the active joint units 421a to 421f so that the purpose of motion set in step S107 may be executed, while also compensating for the gravitational component which cannot be fully compensated for by the gravity compensation mechanisms 460 and 470. In so doing, it is possible to moderate increases in the load on the actuator 430 provided in the active joint units 421b and 421c closer to the root side due to a change in the form of the arm unit 420 by a passive form modification mechanism, and prevent increased bulk of the actuator 430.

6. CONCLUSION

As described above, the support arm apparatus 400 according to the present embodiment is provided with a passive form modification mechanism by which the form of the arm unit 420 may be modified. For this reason, it is possible to modify the movable range of the arm unit 420 in accordance with the content or purpose of the surgical technique. Consequently, it is possible to keep the surgeon's field of view and working space from being obstructed more than necessary, and to keep the arrangement of other equipment inside the operating room from being impeded more than necessary. Also, with the support arm apparatus 400 according to the present embodiment, it is possible to moderate cost increases in order to secure an appropriate movable range, without increasing the degrees of freedom (the number of active joint units) more than necessary.

Additionally, in the support arm apparatus 400 according to the present embodiment, the displacement amount of a passive form modification mechanism can be preset in multiple stages, and in addition, multiple sets of mass property information can be preset, in accordance with a pattern of the form that the arm unit 420 may take. Consequently, at the beginning of a surgical technique, or when a large expansion of the field of view becomes necessary during surgery, a control value of the arm unit 420 can be modified to match the change in the form of the arm unit 420, and increases in the load on the driving control of the arm unit 420 during surgery can be moderated.

Also, in the support arm apparatus 400 according to the present embodiment, passive form modification mechanisms are provided farther towards the root side than the three active joint units 421d to 421f on the front end side which mainly change the imaging direction of the endoscopic device 423 provided as the front end unit. Consequently, the movable range of the arm unit 420 can be adjusted with reduced influence on the control of the direction of the front end unit.

Also, in the support arm apparatus 400 according to the present embodiment, the component portion on the front end side and the component portion on the root side can be separated by a passive form modification mechanism. For this reason, the form of the support arm apparatus 400 can be changed by replacing the configuration portion on the front end side with a different configuration portion made up of different link lengths, for example, and the versatility of the support arm apparatus 400 can be increased further.

Also, in the support arm apparatus 400 according to the present embodiment, by providing gravity compensation mechanisms 460 and 470 for the active joint units 421b and 421c disposed on the root side of the arm unit 420, increased bulk of the actuator 430 provided in the active joint units 421b and 421c is moderated, even in cases in which the intrinsic weight acting on the active joint units 421b and 421c increases due to the inclusion of a passive form modification mechanism.

It should be understood by those skilled in the art that various modifications, combinations, sub-combinations and alterations may occur depending on design requirements and other factors insofar as they are within the scope of the appended claims or the equivalents thereof. Additionally, the exemplary configurations described in the foregoing embodiments may be combined with each other as appropriate, or substitutions may be made.

For example, in the support arm apparatus 400 according to the foregoing embodiment, the displacement amount of a passive form modification mechanism can be preset in multiple stages, and multiple sets of prestored mass property information are used for control in accordance with the pattern of the form of the arm unit 420 which may be set. However, the technology according to an embodiment of the present disclosure is not limited to such an example. In a case in which a passive form modification mechanism can be displaced continuously, instead of using prestored mass property information, the mass property information may also be found by performing computation on the basis of a displacement amount of the passive form modification mechanism detected by a sensor.

Also, the target of application of the technology according to an embodiment of the present disclosure is not limited to the medical field, and may also be fields other than the medical field. For example, the technology according to an embodiment of the present disclosure is also favorably applicable to gravity compensation in an industrial support arm apparatus used for product assembly and inspection steps in a factory. By using the technology according to an embodiment of the present disclosure, in an industrial support arm apparatus, similarly to the embodiments described earlier, it is possible to configure the support arm apparatus more compactly and at a lower weight, and thus advantageous effects such as reduced manufacturing costs and an improved degree of freedom in the installation space can be obtained.

Further, the effects described in this specification are merely illustrative or exemplified effects, and are not limitative. That is, with or in the place of the above effects, the technology according to an embodiment of the present disclosure may achieve other effects that are clear to those skilled in the art from the description of this specification.

Additionally, the present technology may also be configured as below.

(1)
A medical support arm apparatus, including:
a plurality of active joint units that join a plurality of links, and are driven by actuators to allow an attitude of an arm unit made up of the plurality of links to be changed;
a torque sensor that detects a torque acting on the active joint unit; and at least one passive form modification mechanism that allows a form of the arm unit to be changed.

(2)
The medical support arm apparatus according to (1), including:
a sensor that detects a displacement amount of the passive form modification mechanism.

(3)
The medical support arm apparatus according to (1) or (2), in which
the passive form modification mechanism is displaceable by a displacement amount preset in multiple stages.

(4)
The medical support arm apparatus according to any one of (1) to (3), in which
the passive form modification mechanism is a passive slide mechanism.

(5)
The medical support arm apparatus according to any one of (1) to (3), in which
the passive form modification mechanism is a passive joint unit.

(6)
The medical support arm apparatus according to any one of (1) to (5), in which
the arm unit has at least six degrees of freedom or more, and the passive form modification mechanism is disposed farther towards a root side than the at least three active joint units on a front end side of the arm unit.

(7)
The medical support arm apparatus according to any one of (1) to (6), in which
the passive form modification mechanism includes a detachable mechanism that allows the arm unit to be separated into a front end side portion and a root side portion.

(8)
The medical support arm apparatus according to any one of (1) to (7), in which
the at least one active joint unit is provided with a gravity compensation mechanism that compensates for a weight of the arm unit itself.

(9)
The medical support arm apparatus according to any one of (1) to (8), including: an attitude sensor that detects an inclination of the arm unit.

(10)
The medical support arm apparatus according to any one of (1) to (9), in which
a medical tool is supported on a front end part of the arm unit.

(11)
The medical support arm apparatus according to (10), in which
the medical tool is an endoscope or microscope camera.

(12)
The medical support arm apparatus according to any one of (1) to (11), including:
a control unit that conducts whole body cooperative control of the arm unit by driving the actuators provided in the plurality of active joint units.

(13)
The medical support arm apparatus according to (12), in which
the control unit conducts whole body cooperative control on a basis of a displacement amount of the passive form modification mechanism.

(14)
The medical support arm apparatus according to (13), in which
the control unit uses a control value of the whole body cooperative control preset on a basis of the displacement amount of the passive form modification mechanism preset in multiple stages.

(15)
The medical support arm apparatus according to any one of (12) to (14), in which
the control unit controls the actuators to cancel out gravity acting on the arm unit, and also controls the actuators to assist with movement of the arm unit in a direction of a force additionally imparted from outside.

(16)
A medical support system, comprising:
a support arm including
one or more active joints, and
one or more passive coupling mechanisms; and
processing circuitry configured to
obtain information indicating a change due to movement of the one or more passive coupling mechanisms, and
control the one or more active joints based on the obtained information indicating the change.

(17)
The medical support system according to (16), wherein the change is a shift in a center of gravity of the support arm.

(18)
The medical support system according to (16)-(17), wherein the one or more passive coupling mechanisms include at least one passive joint and a passive slide mechanism.

(19)
The medical support system according to (16)-(18), wherein the one or more passive coupling mechanisms have no actuator.

(20)
The medical support system according to (16)-(19), wherein the at least one active joint includes an actuator connected to the processing circuitry.

(21)
The medical support system according to (20), wherein the actuator includes a torque sensor.

(22)
The medical support system according to (16)-(21), wherein the movement of the at least one passive coupling mechanisms is due to user operation.

(23)
The medical support system according to (18), wherein the at least one passive joint is a non-actuated rotary joint.

(24)

The medical support system according to (16)-(23), wherein the support arm is deformable by the movement of the one or more passive coupling mechanisms to assist a surgical procedure requiring a particular configuration of the support arm.

(25)

The medical support system according to (18), wherein the passive slide mechanism of the support arm is positioned between an active joint and a passive joint.

(27)

The medical support system according to (16)-(25), wherein the support arm includes two or more active joints.

(28)

The medical support system according to (16)-(26), further comprising: a medical imaging device, wherein the medical imaging device is coupled to the support arm.

(29)

The medical support system according to (28), wherein the medical imaging device is an endoscope or a surgical microscope.

(30)

The medical support system according to (16)-(29), wherein the one or more passive coupling mechanisms are positioned between two active joints.

(31)

The medical support system according to (16)-(30), wherein the one or more passive coupling mechanisms is disposed further towards a proximal end of the support arm than at least three active joints disposed on a distal end of the support arm when the support arm has at least six degrees of freedom.

(32)

The medical support system according to (16)-(31), wherein the one or more passive coupling mechanisms includes a detachable mechanism dividing the support arm into a distal end and a proximal end.

(33)

The medical support system according to (16)-(32), wherein the one or more passive coupling mechanisms includes a passive mechanism that is displaceable in multiple stages.

(34)

The medical support system according to (16)-(33), wherein the one or more passive coupling mechanisms includes a passive slide mechanism and a sensor that detects a displacement amount of the passive slide mechanism.

(35)

The medical support system according to (16)-(34), wherein the support arm includes a plurality of active joints and the processing circuitry is further configured to control the plurality of active joints using whole body cooperative control in which the plurality of active joints are cooperatively controlled.

(36)

The medical support system according to (18), wherein the information indicating a change is obtained on the basis of a displacement amount of passive slide mechanism or based on a detected change of at least one passive joint.

(37)

The medical support system according to (16)-(36), further comprising an attitude sensor.

(38)

The medical support system according to (16)-(37), further comprising a spring or an elastic body producing a restoring force.

(39)

A medical device, comprising:
processing circuitry configured to
obtain information indicating a change due to movement of one or more passive coupling mechanisms, and
control one or more active joints based on the obtained information indicating the change.

(40)

A medical image processing method, comprising:
obtaining information indicating a change due to movement of one or more passive coupling mechanisms; and
controlling one or more active joints based on the obtained information indicating the change.

REFERENCE SIGNS LIST

100, 400, 600 display system
102 imaging device
100 passive slide mechanism (passive form modification mechanism)
110 rail part
120 slider
121 groove part
130 positioning pin
131*a* to 131*c* positioning hole
140 fixing screw
150 sensor
200 passive joint unit (passive form modification mechanism)
210 movable part
220 base plate
230 positioning pin
231 positioning hole
240 fixing screw
250 encoder
351 control unit
353 whole body cooperative control unit
355 ideal joint control unit
400 medical support arm apparatus
420 arm unit
421*a* to 421*f* active joint unit
422*a* to 422*f* link
423 endoscopic device (front end unit)
428 torque sensor
430 actuator
450 attitude sensor
460, 470 gravity compensation mechanism

The invention claimed is:

1. A medical support system, comprising:
a support arm including
one or more active joints, each of the one or more active joints including an actuator, and
one or more passive coupling mechanisms including a passive joint and a telescopic extension arm, the passive joint having no actuator; and
processing circuitry configured to
obtain information indicating a change due to movement of the one or more passive coupling mechanisms, and
control the actuator of each of the one or more active joints based on the Obtained information indicating the change, wherein
the telescopic extension arm is positioned between (1) an active joint of the one or more active joints on a first side of the telescopic extension arm, and (2) the passive joint on a second side of the telescopic extension arm, the first side being closer to a proximal end of the support arm than a distal end of the support arm, the second side being closer to the distal end of the support arm than the proximal end of the support arm, the medical support system further comprises an attitude sensor configured to detect an inclination of the support arm with respect to a horizontal direction, the support arm is attached to a base, the attitude sensor is positioned between the base and a first active joint of the one or more active joints, the first active joint being positioned on a most proximal end of the support arm, and the processing circuitry is further configured to
calculate gravitational force acting on the support arm based on the inclination of the support arm detected by the attitude sensor, and
execute gravity compensation control for canceling out the gravitational force acting on the support arm, by controlling torque generated by the actuator.

2. The medical support system according to claim 1, wherein the change is a shift in a center of gravity of the support arm.

3. The medical support system according to claim 1, wherein the actuator includes a torque sensor.

4. The medical support system according to claim 1, wherein the movement of the at least one passive coupling mechanisms is due to user operation.

5. The medical support system according to claim 1, wherein the passive joint is a non-actuated rotary joint.

6. The medical support system according to claim 1, wherein the support arm is deformable by the movement of the one or more passive coupling mechanisms to assist a surgical procedure requiring a particular configuration of the support arm.

7. The medical support system according to claim 1, wherein the support arm includes two or more of the active joints.

8. The medical support system according to claim 1, further comprising: a medical imaging device, wherein the medical imaging device is coupled to the support arm.

9. The medical support system according to claim 8, wherein the medical imaging device is an endoscope or a surgical microscope.

10. The medical support system according to claim 1, wherein the one or more passive coupling mechanisms are positioned between two of the active joints.

11. The medical support system according to claim 1, wherein the one or more passive coupling mechanisms is disposed further towards the proximal end of the support arm than at least three active joints disposed on the distal end of the support arm when the support arm has at least six degrees of freedom.

12. The medical support system according to claim 1, wherein the one or more passive coupling mechanisms includes a detachable mechanism dividing the support arm into a side on the distal end and a side on the proximal end.

13. The medical support system according to claim 1, wherein the telescopic extension arm is displaceable in multiple stages.

14. The medical support system according to claim 1, wherein the one or more passive coupling mechanisms includes a sensor that detects a displacement amount of the telescopic extension arm.

15. The medical support system according to claim 1, wherein the support arm includes a plurality of the active joints and the processing circuitry is further configured to control the plurality of the active joints using whole body cooperative control in which the plurality of the active joints are cooperatively controlled.

16. The medical support system according to claim 14, wherein the information indicating the change is obtained based on the displacement amount of the telescopic extension arm detected by the sensor.

17. The medical support system according to claim 1, further comprising a spring or an elastic body producing a restoring force.

* * * * *